United States Patent
Lee et al.

(10) Patent No.: US 10,480,014 B2
(45) Date of Patent: Nov. 19, 2019

(54) METHOD FOR PRODUCING NATURAL RUBBER BY USING RECOMBINANT MICROORGANISM

(71) Applicant: Ajou University Industry-Academic Cooperation Foundation, Suwon-si, Gyeonggi-do (KR)

(72) Inventors: Pyung Cheon Lee, Yongin-si (KR); Jin Ho Kim, Yongin-si (KR)

(73) Assignee: AJOU University Industry-Academic Cooperation Foundation, Suwon-si, Gyeonggi-do (KR)

( * ) Notice: Subject to any disclaimer, the term of this patent is extended or adjusted under 35 U.S.C. 154(b) by 140 days.

(21) Appl. No.: 15/736,931

(22) PCT Filed: Jun. 15, 2016

(86) PCT No.: PCT/KR2016/006334
§ 371 (c)(1),
(2) Date: Dec. 15, 2017

(87) PCT Pub. No.: WO2016/204503
PCT Pub. Date: Dec. 22, 2016

(65) Prior Publication Data
US 2018/0371501 A1 Dec. 27, 2018

(30) Foreign Application Priority Data
Jun. 15, 2015 (KR) .......................... 10-2015-0084038

(51) Int. Cl.
| | |
|---|---|
| *C12P 5/00* | (2006.01) |
| *C12N 15/113* | (2010.01) |
| *C12N 9/90* | (2006.01) |
| *C12N 9/10* | (2006.01) |
| *C07K 14/415* | (2006.01) |
| *C12N 15/63* | (2006.01) |
| *C12N 15/81* | (2006.01) |
| *C12N 15/74* | (2006.01) |
| *C12N 15/70* | (2006.01) |

(52) U.S. Cl.
CPC .............. *C12P 5/00* (2013.01); *C07K 14/415* (2013.01); *C12N 9/1025* (2013.01); *C12N 9/90* (2013.01); *C12N 15/113* (2013.01); *C12N 15/63* (2013.01); *C12N 15/70* (2013.01); *C12N 15/74* (2013.01); *C12N 15/81* (2013.01); *C12Y 205/01031* (2013.01); *C12Y 503/03002* (2013.01)

(58) Field of Classification Search
None
See application file for complete search history.

(56) References Cited

PUBLICATIONS

Asawatreratanakul et al. (Molecular cloning, expression and characterization of cDNA encoding cis-prenyltransferases from Hevea brasiliensis, Eur. J. Biochem. 270, 4671-4680 (2003)).*

* cited by examiner

*Primary Examiner* — Suzanne M Noakes
*Assistant Examiner* — Jae W Lee
(74) *Attorney, Agent, or Firm* — Vorys, Sater, Seymour and Pease LLP; Mih Suhn Koh

(57) ABSTRACT

A method for producing natural rubber by using a recombinant microorganism is disclosed, the method comprising: (a) manufacturing an expression vector capable of expressing a gene encoding a cis-prenyltransferase, which is a guayule-derived natural rubber synthetase represented by the amino acid sequence of SEQ ID NO: 2 or a *Hevea brasiliensis*-derived natural rubber synthetase represented by the amino acid sequence of SEQ ID NO: 6, and an expression vector capable of expressing a gene coding for a natural rubber precursor synthetase; (b) transforming a host microorganism with the expression vector; (c) culturing the transformed host microorganism; and (d) separating natural rubber from the cultured transformed host microorganism. The natural rubber obtained by the method has a white powder form identical to that of natural rubber, and shows an FT-IR spectrum pattern extremely similar to that of natural rubber.

16 Claims, 14 Drawing Sheets

Specification includes a Sequence Listing.

METHOD FOR PRODUCING NATURAL RUBBER BY USING RECOMBINANT MICROORGANISM

SEQUENCE LISTING

The Sequence Listing submitted in text format (.txt) filed on Dec. 15, 2017, named "SequenceListing.txt", created on Dec. 13, 2017 (13.9 KB), is incorporated herein by reference.

TECHNICAL FIELD

The present invention relates to a method for producing natural rubber by use of a recombinant microorganism.

BACKGROUND ART

Natural rubber, which is a polymer (cis-1,4-polyisoprene, m.w.≥1,000 kDa) composed of 320-35,000 isoprene molecules, is one of the most important polymers obtained from plants and is used as a natural material for a variety of products including medical devices, tires, belts, etc. Natural rubber is synthesized by sequentially adding isopentenyl diphosphate to a priming molecule under catalysis by a class of enzymes, called prenyltransferases.

Natural rubber exhibits excellent practical features in elasticity, flexibility, resilience, and wear resistance which cannot be compared to those of synthetic rubber. As many as about 2,500 plants including guayule (*Parthenium argentatum*) and *Ficus carica* are reported to produce natural rubber, but the industrially available sole source of natural rubber is the rubber tree (*Hevea brasiliensis*), which produces natural rubber with high molecular weights. Most of the natural rubber used in practical life is known to be obtained from the rubber tree.

However, the rubber tree is of low genetic diversity associated with vulnerability to the attack of pest insects, and the danger that the latex fluid therefrom might act as an allergen to human bodies has been raised (Mooibroek h, Cornish k. Microbiol. Biotechnol. 53:355-365 (2000)). For such reasons, efforts have been attempted to biosynthesize natural rubber with the aid of genetic recombination technology in addition to searching for alternative plants producing natural rubber. For example, genes associated with the biosynthesis of natural rubber, such as prenyltransferase in the rubber tree, were isolated and reported (PCT WO/01/21650; Shimizu et al., J. Biol. Chem. 273:19476-19481 (1998); Apfel et al., J. Bacteriol. 181:483-492 (1999); Sato et al., Mol. Cell. Biol. 19:471-483 (1999); AUTHORS Kim, et al., J. Exp. Bot. 55 (396), 377-385 (2004)), and an attempt was made to biosynthesize natural rubber by use of genetic recombination technology in *Arabidopsis thaliana* (PCT/US2000/25856).

The present invention also discloses a method for producing natural rubber by use of a recombinant microorganism such as *E. coli*.

DISCLOSURE

Technical Problem

An object of the present invention is to provide a method for producing natural rubber by use of a recombinant microorganism.

Another object of the present invention to provide a recombinant microorganism having ability to produce natural rubber.

Other and concrete objects of the present invention will be proposed below.

Technical Solution

According to the intensive and thorough research of the present inventors, as will be evidenced in the following Example Section, when guayule-derived gene (GenBank accession no. AF541942.1, SEQ ID NO: 1) coding for cis-prenyltransferase (GenBank accession no. AAQ11374, SEQ ID NO: 2), which is a natural rubber synthase in guayule, and an *E. coli*-derived gene (GenBank accession no. NC_000913 (REGION: 194906 . . . 195664), SEQ ID NO: 3) coding for undecaprenyl (UDP) pyrophosphate synthase (GenBank accession no. WP_032359110, SEQ ID NO: 4), which is a natural rubber precursor synthase in *E. coli* were introduced together into *E. coli*, the resulting product from the *E. coli* was found to have the same feature of white powder as natural rubber, exhibit FT-IR spectral patterns extremely similar to those of natural rubber (polyisoprene with a molecular weight >38,000, Sigma Aldrich), contains double bonds and alkanes as in natural rubber, as measured by NMR spectrophotometry, and include a compound with a molecular weight of 500,000 Da therein, as measured by GPC analysis.

In addition, as will be evidenced in the following Example Section, when a *Hevea brasiliensis*-derived gene (GenBank accession no. AY124466, SEQ ID NO: 5) coding for cis-prenyltransferase (GenBank accession no. AAM92882, SEQ ID NO: 6), which is a natural rubber synthase in the rubber tree (*Hevea brasiliensis*) and an *E. coli*-derived gene (SEQ ID NO: 3) coding for UDP pyrophosphate synthase (GenBank accession no. WP_032359110, SEQ ID NO: 4), which is a natural rubber precursor synthase in *E. coli*, were introduced together into and expressed simultaneously in *E. coli*, the same white powder as natural rubber was also obtained.

Further, it was found that expression of a gene (GenBank accession no. NC_000913.3 (REGION: 3033065 . . . 3033613), SEQ ID NO: 7) coding for isopentenyl diphosphate isomerase (GenBank accession no. NP_417365.1, SEQ ID NO: 8), which controls an amount of the main material isopentenyl diphosphate in the biosynthesis process of natural rubber precursors in *E. coli*, together with the gene coding for the natural rubber synthase in guayule or *Hevea brasiliensis* and the gene coding for the natural rubber synthase in *E. coli*, led to an increase in the production of natural rubber.

For reference, as will be identified in the Comparative Example Section, when only the cis-prenyltransferase gene of guayule or the gene encoding the *Hevea brasiliensis*-derived cis-prenyltransferase, which is known to have the same activity as in the cis-prenyltransferase of guayule, was expressed in *E. coli*, no white powder was obtained. No polymer products were produced, either, as measured by GPC analysis.

These experiment results indicate that the expression of guayule- or *Hevea brasiliensis*-derived (or isolated, originated) cis-prenyltransferase gene is preferable for the production when conducted in combination with a gene encoding a natural rubber precursor synthase, for example, an *E. coli*-derived UDP pyrophosphate synthase gene and is very advantageous in increasing the production yield when conducted additionally in combination with an isopentenyl diphosphate isomerase gene of *E. coli*.

In consideration of the foregoing, the method for producing natural rubber by using recombinant microorganisms according to the present invention comprises the steps of: (a) constructing an expression vector capable of expressing a gene coding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, or a functional equivalent thereof, and an expression vector capable of expressing a gene coding for a natural rubber precursor synthase, for example, UDP pyrophosphate synthase, which is an *E. coli*-derived natural rubber precursor synthase having the amino acid sequence of SEQ ID NO: 4, or a functional equivalent thereof; (b) transforming the expression vectors into a host microorganism; (c) culturing the transformed host microorganism; and (d) isolating natural rubber from a culture of the transformed host microorganism.

In particular some embodiments, an expression vector capable of a gene coding for an *E. coli*-derived isopentenyl diphosphate isomerase having the amino acid sequence of SEQ ID NO: 8, or a functional equivalent thereof is constructed in step (a) so as to increase the production yield, and co-transfected into the host microorganism in step (b).

In the method of the present invention, the cis-prenyltransferase gene, that is, the natural rubber synthase gene of guayule, and the UDP pyrophosphate synthase gene may encode respectively the proteins composed of the amino acid sequences of SEQ ID NOS: 2 and 3 or functional equivalents thereof. As used herein, the term "functional equivalent" refers to a protein that still retains the intrinsic function (e.g., cis-prenyltransferase or UDP pyrophosphate synthase activity) even though some amino acids are substituted. By way of example, even if the hydrophobic amino acid alanine is substituted by a different hydrophobic amino acid, i.e., glycine, the protein can still retain and exert its intrinsic function. For other examples, the protein can retain and exert its intrinsic function even if substitution occurs between negatively charged amino acids, e.g., glutamic acid and aspartic acid or between positively charged amino acids, e.g., arginine and lysine. The functional equivalent may be defined as amino acid sequence homology in protein terms. In detail, the functional equivalent may be defined as a protein sharing a sequence homology of 95% or higher with the amino acid sequence of SEQ ID NO: 3 or 4, with increasing preference for a homology of 95%, 96%, 97%, 98%, and 99% in that order. In addition, the definition of the functional equivalent is true of base sequence homology at a gene level. Concretely, the functional equivalent may be defined as a gene sharing a sequence homology of 90% or higher with the base sequence of SEQ ID NO: 1 or 2, with increasing preference for 91%, 92%, 93%, 94%, 95%, 96%, 97%, 98%, and 99% in that order. Genes with such sequence homology may be chemically synthesized or may be obtained by isolation from particular organisms anchoring the corresponding genes, and amplification.

In some embodiments of the present invention, one expression vector may be constructed to carry all the cis-prenyltransferase gene, the UDP pyrophosphate synthase gene, and/or the isopentenyl diphosphate isomerase gene, introduced into a host microorganism, and allowed to express all the genes although it is described in the following Example Section that respective expression vectors are constructed to carry the genes.

The term "expression vector" as used herein, refers to a DNS construct capable of expressing a target gene (a cis-prenyltransferase gene, a UDP pyrophosphate synthase, etc., in the present invention) in a host microorganism. When introduced into a host microorganism, the expression vector replicates independently of the genome of the host microorganism to function (express the target gene), or integrates into the genome of the host microorganism before replicating to function.

In the present invention, the expression vector may be a nucleic acid in the form of, for example, a plasmid, a cosmid, a phagemid, or a phage, and vectors suitable for host microorganisms may be purchased from commercially available ones, or may be obtained by modifying commercially available ones. For example, when *E. coli* is used as a host microorganism, selection may be made of pUC19, pSTV28, pBBR1MCS, pBluscriptII, pBAD, pTrc99a, pET, pACYC184, pBR322, pJE101, pJE102, and pJE103.

A large amount of documents on expression vector organization including recombinant DNA technology has been accumulated in the field. For instance, reference may be made to [Sambrook et al., Molecular Cloning, A Laboratory Manual, Cold Spring Harbor Laboratory Press, (2001)], [F. M. Ausubel et al, Current Protocols in Molecular Biology, John Wiley amp; Sons, Inc. (1994)], and [Marston, F. (1987) DNA Cloning Techniques]. All literatures cited herein are incorporated by reference although not explicitly stated.

The expression vector includes the target genes cis-prenyltransferase gene, UDP pyrophosphate synthase gene, and/or isopentenyl diphosphate isomerase gene, and regulatory sequences that are operatively linked to the target genes and affect the transcription and translation of the target objects.

Among such regulatory sequences are typically a promoter, a transcription stop signal sequence (polyadenylation signal), and the like. The term "operatively linked", as used in this context, is intended to mean that a linkage occurs such that the transcription and/or translation of a certain gene is affected. For example, if a promoter has an influence on the transcription of a certain gene linked thereto, the promoter and the gene are operatively linked to each other.

As used herein, the term "promoter" conforms to the meaning typically known in the art and refers concretely to a nucleic acid sequence which is located upstream (towards the 5' region) of a transcription initiation site for a particular gene and includes a binding site for DNA-dependent RNA polymerase, a transcription initiation site, and a transcription factor binding site, thus functioning to control the transcription of one or more genes. A promoter includes an essential part located upstream of a transcription initiation site, such as a Pribnow box (located generally at $-10$ position relative to a transcription initiation site $(+1)$) and a Hogness box (located generally at $-35$ position relative to a transcription initiation site $(+1)$), if originating from prokaryotes and, such as a TATA box (located generally at $-20$ to $-30$ positions relative to a transcription initiation site $(+1)$), a CAAT box (located generally at about $-75$ position relative to a transcription initiation site $(+1)$), an enhancer, a transcriptional repressor, etc., if derived from eukaryotes.

So long as it is able to express a target gene linked thereto, any promoter, whether constitutive (active in all circumstances to induce expression in particular organisms) or inducible (activated in response to a specific exogenous stimulus to induce the expression of a target gene), may be used. Preferable is a promoter suitable to a particular host microorganism. For example, a preference may be made for promoters such as T7A1, T7A2, T7A3, λpL, λpR, lac, lacUV5, trp, tac, trc, phoA, rrnB, and 1PL when *E. coli* is used as a host microorganism, and promoters such as GAL1, GAL10, ADH1, TDH3, and PGK when a yeast is used as a host microorganism.

The expression vector includes a terminator sequence, which signals the termination of transcription, in addition to the promoter. Acting to direct the addition of poly(A) (polyadenylation signal), a terminator sequence increases the completeness and efficiency of transcription. Terminator sequences suitable to host microorganisms are known in the art. For example, the tac terminator sequence or the rrnB terminator sequence may be available when *E. coli* is used as a host microorganism while the ADH1 terminator sequence may be used in yeast.

Further, the expression vector may include a selection marker gene. A selection marker gene encodes a character which allows for the section of a host microorganism having the marker gene. In general, an antibiotic resistance gene is used. Examples of available antibiotic resistance genes include puromycin resistance gene (e.g., *Streptomyces alboniger*-derived puromycin N-acetyl transferase gene), neomycin resistance gene (e.g., *Streptomyces fradiae*-derived aminoglycoside phosphotransferase gene), hygromycin resistance gene (*Streptomyces hygroscopicus*-derived hygromycin phosphotransferase gene), bleomycin resistance gene (*Streptomyces verticillus*-derived bleomycin-binding protein), blasticidin resistance gene (e.g., *Streptomyces verticillium*-derived blasticidin S-acetyltransferase gene), hygromycin resistance gene (e.g., *Escherichia coli*-derived aminocyclitol phosphotransferase gene), and ampicillin resistance gene (β-lactamase gene).

Alternatively, the selection marker gene may be thymidylate synthase gene, thymidine kinase gene, or dihydrofolate reductase. These genes make it possible to select host microorganisms having the corresponding genes in media lacking specific ingredients (Kaufman R. J., Methods Enzymol 185, 537-56 (1990)).

In the method of the present invention, the expression vector may further include a restriction enzyme recognition site for ease in cloning a target gene.

In the method of the present invention, the step (a) of constructing an expression vector is followed by the step (b) of transforming the expression vector into a host microorganism.

Transformation is the genetic alteration of a host cell resulting from the direct uptake and incorporation of exogenous genetic material. After introduced into the host cell, the exogenous genetic material may exist independently of the host cell genome or may be incorporated into the host cell genome. Examples of the exogenous genetic material include a homogenous gene and a heterogeneous gene. Herein, the term "homogenous gene" refers to a gene intrinsic to the host microorganism or the same species, and the term "heterogeneous gene" refers to a gene which does not exist in an organism to be transformed therewith. In the method of the present method, for example, when a cis-prenyltransferase gene, which is a guayule-derived natural rubber synthase gene, and a UDP pyrophosphate synthase gene, which is an *E. coli*-derived natural rubber precursor synthase gene, are introduced into *E. coli*, the cis-prenyltransferase, which is a guayule-derived natural rubber synthase, is a heterogeneous gene while the UDP pyrophosphate synthase gene, which is an *E. coli*-derived natural rubber precursor synthase gene, is a homogeneous gene.

Methods of transforming exogenous genes into host organisms are known in the art, and of the known methods, any one may be selected and used in the present invention.

For example, transformation may be accomplished by use of a $CaCl_2$ method, a Hanahan method, an electroporation method, or a calcium phosphate precipitation method when a prokaryote such as *E. coli* is used as a host microorganism, and a microinjection method, a calcium phosphate precipitation method, an electroporation method, a liposome-mediated transfection method, a DEAE-dextran treatment method, or a gene bombardment method may be available for a eukaryotic host microorganism such as yeast. With regard to details of transformation, reference may be made to the following literatures: Cohen, S. N. et al., Proc. Natl. Acac. Sci. USA, 9:2110-2114(1973); Hanahan, D., J. Mol. Biol., 166:557-580(1983); Dower, W. J. et al., Nucleic. Acids Res., 16:6127-6145(1988); Capecchi, M. R., Cell, 22:479(1980); Graham, F. L. et al., Virology, 52:456(1973); Neumann, E. et al., EMBO J., 1:841(1982); Wong, T. K. et al., Gene, 10:87(1980); Gopal, Mol. Cell Biol., 5:1188-1190 (1985); Yang et al., Proc. Natl. Acad. Sci., 87:9568-9572 (1990); Maniatis et al., Molecular Cloning: A Laboratory Manual, Cold Spring Harbor Laboratory (1982); Hitzeman et al., J. Biol. Chem., 255, 12073-12080 (1980); and Luchansky et al Mol. Microbiol. 2, 637-646 (1988).

A host microorganism available in the method of the present invention may be prokaryotic or eukaryotic. Prokaryotes may be Gram-positive cells or Gram-negative cells. In detail, *Escherichia* spp., *Salmonella* spp., *Shigella* spp., *Enterobacter* spp., *Serratia* spp., *Erwinia* spp., *Serratia* spp., *Pseudomonas* spp., *Caulobacter* spp., *Synechocystis* spp. (e.g., *Synechocystis* species PCC 6803 or *Synechocystis* species PCC 6301), *Synechococcus* spp., *Bacillus* spp. (e.g., *Bacillus brevis, Bacillus subtilis, Bacillus thuringienesis*, etc.), *Lactococcus* spp. (e.g., *Lactococcus lactis*), *Streptomyces* spp. (e.g., *Streptomyces lividans, Streptomyces ambofaciens, Streptomyces fradiae, Streptomyces griseofuscus*), *Rhodococcus* spp. (e.g., *Rhodococcus erythropolis*), *Corynebacterium* spp. (e.g., *Corynebacterium gluamicum*), and *Mycobacterium* spp. (e.g., *Mycobacterium smegmatis*) may be used.

Available eukaryotes may be yeast cells including, for example, *Pichia* spp. (e.g., *Pichia pastoris*), *Saccharomyces* spp. (e.g., *Saccharomyces cerevisiae*), *Hansenula* spp. (e.g., *Hansenula polymorpha*), *Kluyveromyces* spp. (e.g., *Kluyveromyces lactis*), and *Schizosaccharomyces* spp. (e.g., *Schizosaccharomyces pombe*).

Preferable is *Escherichia coli*. When used for expression, *E. coli* has an advantage over other host microorganisms in terms of cost and yield. *E. coli* suitable for the high-yield expression of a target gene may be exemplified by *E. coli* W3110, *E. coli* BL21, BL21(DE3), DH1, DH4I, DH5, DH5I, DH5IF', DH5IMCR, DH10B, DHIOB/p3, DH1 IS, C600, HB101, JM101, JM105, JM109, JM110, K38, RR1, Y1088, Y1089, CSH18, ER1451, ER1647, NovaBlue, DH5α, K12 RV308, K12 C600, K-12, MG1655, and HB101 strains. For more details, reference may be made to the literature (Brown, Molecular Biology Labfax, Academic Press (1991)), the entire disclosure of which is hereby incorporated by reference.

In order for a target protein to exert and maintain its function in *E. coli*, an *E. coli* strain which lacks proteinase activity may be preferably used as a host microorganism. For more details, reference may be made to the literature (Gottesman, S., Gene Expression Technology: Methods in Enzymology 185, Academic Press, San Diego, Calif., 119-128 (1990)).

In addition, in order to express a target gene at high yield in *E. coli*, the sequence of the target gene may be optimized to codons to which *E. coli* prefers. For this, reference may be made to the literature (Wada et al., Nucleic Acids Res. 20:2111-2118 (1992)).

According to the method of the present invention, the host microorganism, after transformed as described above, is cultured to induce the production of natural rubber.

As a rule, a host microorganism is cultured in a medium containing a carbon source, a nitrogen source, and trace elements.

Preferably, a carbon source is sugar such as a monosaccharide, a disaccharide, or a polysaccharide. For example, glucose, fructose, mannose, galactose, ribose, sorbose, ribulose, lactose, maltose, sucrose, raffinose, and starch may be used. Composite compounds such as molasses or byproducts resulting from sugar refining processes may be also available. According to circumstances, it may be advantageous to use a composition of various sugar ingredients. Some host microorganism may prefer oils, such as soybean oil and sunflower oil, or organic acids, such as acetic acid, as a carbon source.

As a nitrogen source, inorganic nitrogen compounds, organic nitrogen compounds, or composite compounds containing both of them may be used. For example, the inorganic nitrogen compounds include ammonia, ammonium salts (e.g., ammonium sulfate, ammonium chloride, ammonium phosphate, ammonium carbonate, ammonium nitrate, etc.), and nitrate. Urea and amino acids may be exemplified for the organic nitrogen compounds, and soybean meal, soybean proteins, yeast extracts, and meat extract fall within the scope of the composite compounds.

Examples of the trace element include calcium, magnesium, sodium, cobalt, molybdenum, potassium, manganese, zinc, copper, iron, phosphor, and sulfur. These trace elements may be added in the form of salts to media, optionally together with a chelating agent, such as catechol, citric acid, etc., for enhancing the solubility of the trace elements and maintaining a solution condition.

A medium for culturing a host microorganism may include growth promoters, such as biotin, riboflavin, thiamine, folic acid, nicotinic acid, pantothenate, pyridoxine, etc.

For optimization of medium compositions, reference may be made to the literature (Applied Microbiol. Physiology, A Practical Approach (Editors P. M. Rhodes, P. F. Stanbury, IRL Press (1997) pp. 53-73, ISBN 0 19 963577 3), the entire disclosure of which is hereby incorporated by reference.

A medium is preferably sterilized before inoculation of host microorganism thereto in order to prevent the growth of unnecessary microorganisms. Sterilization methods are known in the art, and a suitable one may be selected from among known sterilization methods. For example, autoclaving, UV sterilization, and the like may be used.

As for a culture temperature, its range may be between 15° C. and 45° C., preferably between 25° C. and 40° C., and more preferably between 35 and 37° C. The medium has a pH of 5 to 8.5 and preferably about 7.0. The pH of the medium may be adjusted by adding an alkaline compound such as sodium hydroxide, potassium hydroxide, aqueous ammonia, etc., or an acidic compound such as phosphoric acid, sulfuric acid, etc., to the medium while culturing is in progress. An antifoaming agent such as fatty acid polyglycol ester may be added to remove bubbles formed during cultivation. A material having a selection effect, such as an antibiotic mentioned above, may be added to the medium to stably proliferate only the transformed microorganisms.

An aerobic condition or an anaerobic condition may be advantageously established according to the growth feature of the host microorganism.

Cultivation may be conducted in a batchwise, semi-batchwise, or continuous manner.

Preferably, cultivation is continued until a desired product reaches a maximum. Such a culturing time differs from a host microorganism to another. Optimum culturing times according to host microorganisms may be determined theoretically and experimentally within the ordinary knowledge of a person skilled in the art.

With regard to suitable culturing methods according to host microorganisms in addition to the foregoing, reference may be made to the following literatures: Bioprozeβtechnik 1. Einfuhrung in die Bioverfahrenstechnik [Bioprocess technology 1. Introduction to Bioprocess technology] (Gustav Fischer Verlag, Stuttgart, 1991); Bioreaktoren and periphere Einrichtungen [Bioreactors and peripheral equipment] (Vieweg Verlag, Brunswick/Wiesbaden, 1994); and Manual of Methods for General Bacteriology (Washington D.C., USA, 1981), issued by the American Society for Bacteriology.

Following cultivation until a maximum of a desired product is achieved, the recovery of natural rubber from the culture is performed. For recovery of natural rubber, the host cells may be preferably lysed by ultrasonication.

Extraction of natural rubber form a culture is known in the art and, for example, a PHA method, a PHB method, etc. may be used. For more details, reference may be made to the literature (Alejandro et al., Microb Ecol. 56, 112-120 (2008)).

In another aspect thereof, the present invention is concerned with a recombinant microorganism transformed with (i) an expression vector capable of expressing a gene coding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, or a functional equivalent thereof, and (ii) an expression vector capable of expressing a gene coding for UDP pyrophosphate synthase, which is an *E. coli*-derived natural rubber precursor synthase having the amino acid sequence of SEQ ID NO: 4, or a functional equivalent thereof.

Contemplated according to a further aspect of the present invention is a recombinant microorganism that is established by further introducing into the transformed recombinant microorganism an expression vector capable of a gene coding for an *E. coli*-derived isopentenyl diphosphate isomerase having the amino acid sequence of SEQ ID NO: 8.

The recombinant microorganism of the present invention has an ability to produce natural rubber. The recombinant microorganism of the present invention can be prepared, stored, and distributed in a freeze dried form.

In accordance with another aspect thereof, the present invention provides a combination of (i) an expression vector capable of expressing a gene coding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, or a functional equivalent thereof, and (ii) an expression vector capable of expressing a gene coding for UDP pyrophosphate synthase, which is an *E. coli*-derived natural rubber precursor synthase having the amino acid sequence of SEQ ID NO: 4, or a functional equivalent thereof.

The combination may further include an expression vector capable of a gene coding for an *E. coli*-derived isopentenyl diphosphate isomerase having the amino acid sequence of SEQ ID NO: 8, or a functional equivalent thereof.

According to another aspect thereof, the present invention provides an expression vector capable of expressing (i) a gene coding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, or a functional equivalent thereof, and (ii) a gene coding for UDP pyrophosphate synthase, which is an *E. coli*-derived natural rubber precursor synthase having the amino acid sequence of SEQ ID NO: 4, or a functional equivalent thereof.

The expression vector may further carry a gene coding for an *E. coli*-derived isopentenyl diphosphate isomerase having the amino acid sequence of SEQ ID NO: 8 so as to express the gene.

The expression vector of the present invention may be introduced into a host microorganism to usefully produce the production of natural rubber.

In relation to the recombinant microorganism and expression vectors of the present invention, functional equivalents, regulatory sequences, and host microorganisms are as defined for the method for producing natural rubber according to the present invention.

Advantageous Effects

As described hitherto, the present invention provides a method for producing natural rubber by using a recombinant microorganism. The natural rubber obtained according to the method of the present invention has the same feature of white powder as the naturally occurring natural rubber, with extreme similarity in FT-IR spectrum patterns therebetween. Therefore, the natural rubber obtained according to the method of the present invention is expected to have physical properties identical or similar to those of naturally occurring natural rubber.

BEST MODE TO CARRY OUT THE PRESENT INVENTION

A detailed description will be given of the present invention with reference to Examples. The following Examples are given only to illustrate the present invention, but should not be construed to limit the present invention.

<EXAMPLES> PRODUCTION OF NATURAL RUBBER USING RECOMBINANT STRAIN

Figure 1:
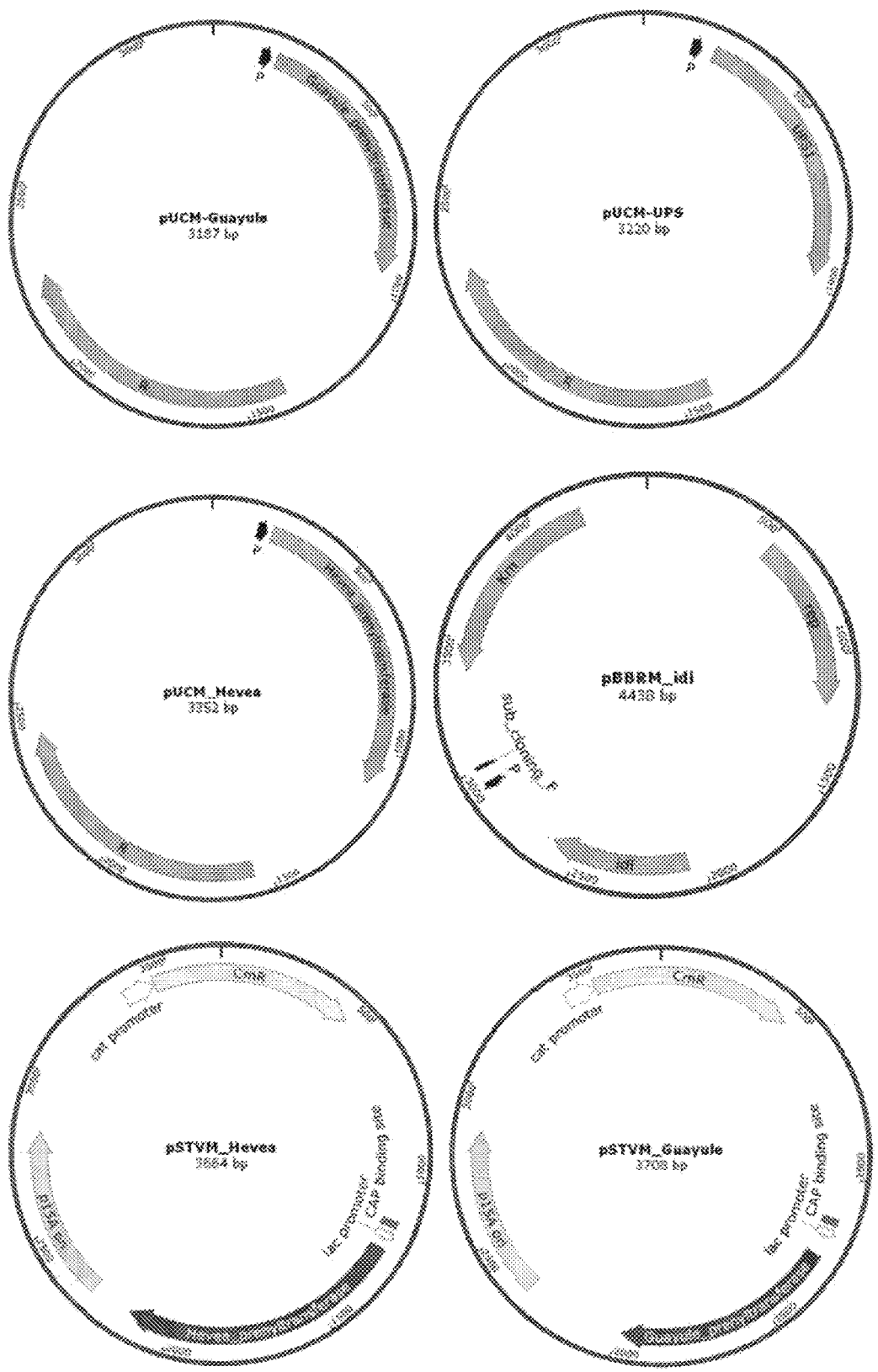
FIG. 1 shows schematic diagrams of vectors used for the production of natural rubber in the recombinant microorganism of the present invention.

<Example 1> Production of Natural Rubber Using Recombinant Strain Having Guayule-Derived Natural Rubber Synthase Gene and *E. coli*-Derived Natural Rubber Precursor Synthase Gene Introduced Thereinto <Example 1-1> Preparation and Cultivation of Recombinant Strain and Production of Natural Rubber For the production of natural rubber, first, the chemical synthesis of both a guayule-derived gene (GenBank accession no. AF541942.1, SEQ ID NO: 1) encoding guayule cis-prenyltransferase (GenBank accession no. AAQ11374, SEQ ID NO: 2), which is a natural rubber synthase, and an *E. coli*-derived gene (GenBank accession no. NC_000913 (REGION: 194906 . . . 195664), SEQ ID NO: 3) encoding UDP pyrophosphate synthase (GenBank accession no. WP_032359110, SEQ ID NO: 4), which is an *E. coli* natural rubber was entrusted to COSMO Genetech (Seoul, Korea). Then, the two synthesized genes were cloned into respective pUCM expression vectors to construct pUCM-guauly and pUCM-UPS, which were both under the control of the constitutive lac promoter (FIG. 1). Since the use of two respective different expression vectors is advantageous for the simultaneous expression of two genes, the guayule cis-prenyltransferase gene in pUCM-guauly was transferred to a pSTVM vector to construct pSTVM-guauly (FIG. 1). In this regard, the lac promotor and the terminator of pUCM-guauly were also cloned into the pSTVM vector having an inducible promoter so as to constitutively express the guayule cis-prenyltransferase gene. pUCM-UPS and pSTVM-guauly were introduced into *E. coli* to produce natural rubber. For example, the pSTVM was in-house constructed by removing the lac promoter from pSTV28 vector (Lot No. 3331, TAKARA, Japan).

Concrete processes are as follows.

For use in cloning an *E. coli*-derived gene coding for UDP pyrophosphate synthase, a forward primer GCCG<u>TCTAGA</u>AGGAGGATTACAAAATG (SEQ ID NO: 9) and a reverse primer <u>GGAATTC</u>TCAGGTGTTTCA (SEQ ID NO: 10) which have an XbaI and an EcoRI restriction enzyme site, respectively (underlined in the sequences), were synthesized. Likewise, an XbaI and an EcoRI restriction enzyme site were respectively introduced into a forward primer TCTAGAAGGAGGATTACAAAATGGCCGAACCTGAATC (SEQ ID NO: 11) and a reverse primer GAATTCCTAACCACTTTGACCAACCG (SEQ ID NO: 12) (underlined in the sequences) for cloning a guayule-derived gene coding for cis-prenyltransferase. PCR was performed with the primers to amplify the corresponding genes. The PCR products were cloned into respective pUCM vectors using the restriction enzymes to construct pUCM-guauly and pUCM-UPS. Subsequently, a forward primer CCCAAGCTTCCGACTGGAAAGCG (SEQ ID NO: 13) and a reverse primer CGGGATCCCGGTGTGAAATACCG (SEQ ID NO: 14) were synthesized from pUCM-guauly to contain a HindIII and a BamHI restriction site (underlined in the sequences), respectively, for use in constructing pSTVM-guauly. Together with the gene, a lac promoter, which is a constitutive expression promoter of pUCM-guauly, and a terminator were amplified by PCR using the primers, and the PCR product thus obtained was cloned into a PSTVM vector using the restriction enzymes to construct pSTVM-guauly. The expression vectors were together introduced into *Escherichia coli* XL1-blue strain by electroporation, followed by selecting the transformed *E. coli* with the aid of antibiotics ampicillin (100 µg/L) and chloramphenicol (100 µg/L). In this regard, the transformants were spread on LB agar plates and selection was made of growing strains. The selected *E. coli* was inoculated into a TB medium containing tryptone 12 g/L, yeast extract 24 g/L, and glycerol 1 g/L, and cultured at 30° C. and 250 rpm for 24 hrs.

After culturing, a PHB extraction method (Alejandro et al., Micro Ecol, 56, 112-120 (2008)) was used to extract rubber from the recombinant *E. coli*. In detail, the cultured cells were separated from the medium by centrifugation and transferred into a 50-ml conical tube which was then filled with 400 ml of absolute ethanol (100%). The cells were lysed by sonication (pulse 40%, time 30 min, pulse-on 5 s, pulse-off 15 s). Following cell lysis, centrifugation separated cell debris from ethanol. Only the cell debris was obtained, mixed with 50 ml of acetone, and incubated for 15 min to remove impurities such as fatty acids. After removal of the impurities, the remaining cell debris was harvested and pooled. The pooled cell debris was mixed with 50 ml of toluene and left for 12 hrs to extract rubber.

After extraction of rubber from the transformed *E. coli*, the powder dried by removal of the extraction solvent was photographed. The image of dried powder was given, together an image of the control natural rubber polyisoprene (molecular weight >38000, Sigma-Aldrich, USA) (upper: dried powder extract from transformed *E. coli*, lower: polyisoprene isolated from the rubber tree). The dried powder extracted from the transformed *E. coli* was seen white as in the control polyisoprene.

<Example 1-2> FT-IR Spectroscopy Analysis

Figure 3:
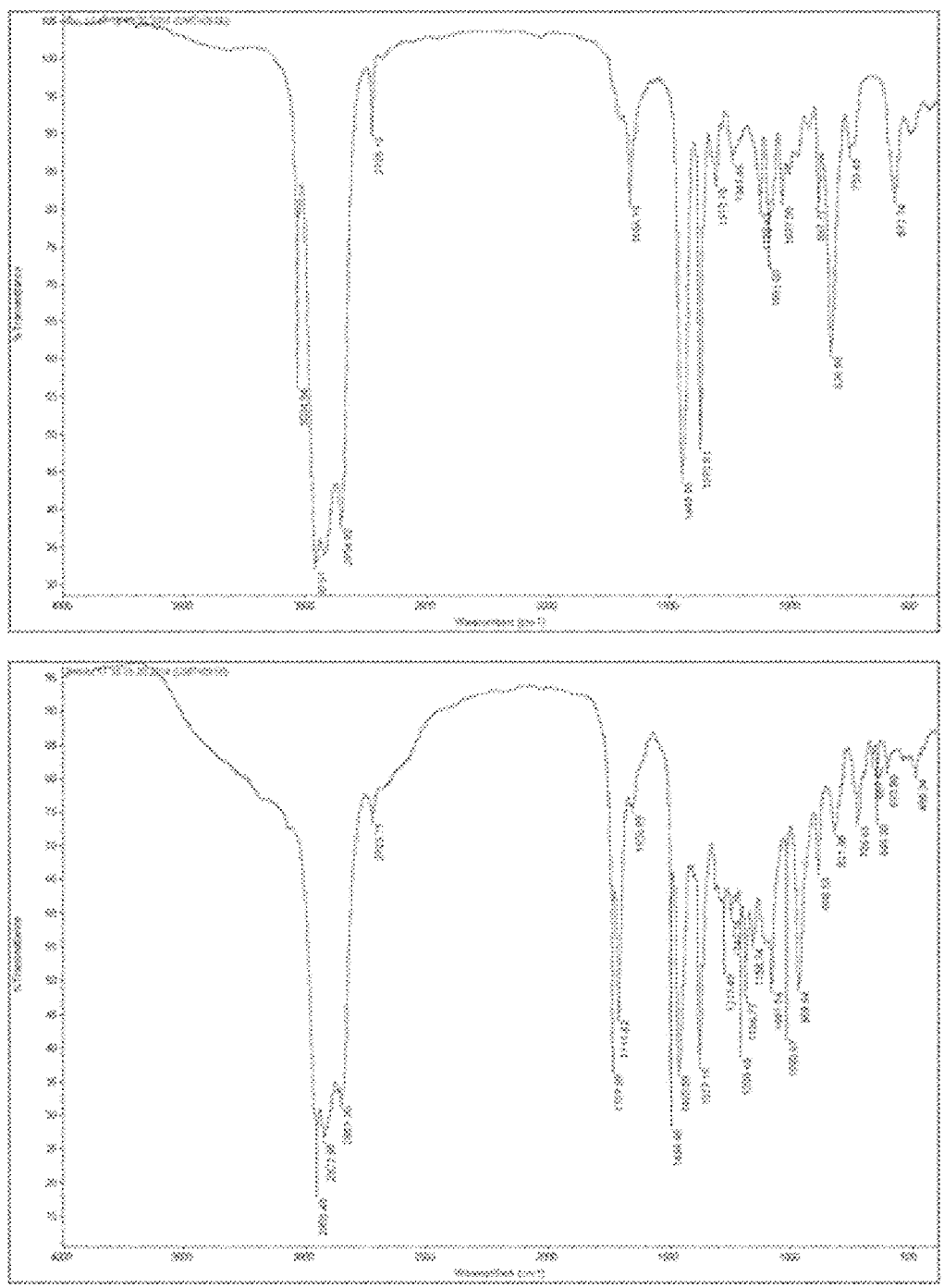
FIG. 3 shows FT-IR spectra of the natural rubber obtained from the recombinant microorganism of the present invention and the control natural rubber (polyisoprene).

FR-IR spectra were obtained from dried powder extracted from the *E. coli* and the control polyisoprene, using an infrared spectrophotometer (Thermo, Nicolet 6700), and are depicted in FIG. 3. In detail, a specimen was dissolved in acetone, and aliquoted at an amount of 50 µl into quartz cells. After drying at room temperature for 2-3 min, a spectrum was obtained by use of a FT-IR spectrophotometer. As a control, polyisoprene purchased from Sigma Aldrich was dissolved in acetone and used in a comparative test.

With reference to FIG. 3, the dried powder extracted from the *E. coli* was observed to show spectral patterns very similar to those of the control polyisoprene (upper: polyisoprene of natural rubber purchased from Sigma Aldrich, lower: natural rubber produced by *E. coli*).

<Example 1-3> NMR Spectral Analysis

Figure 4:
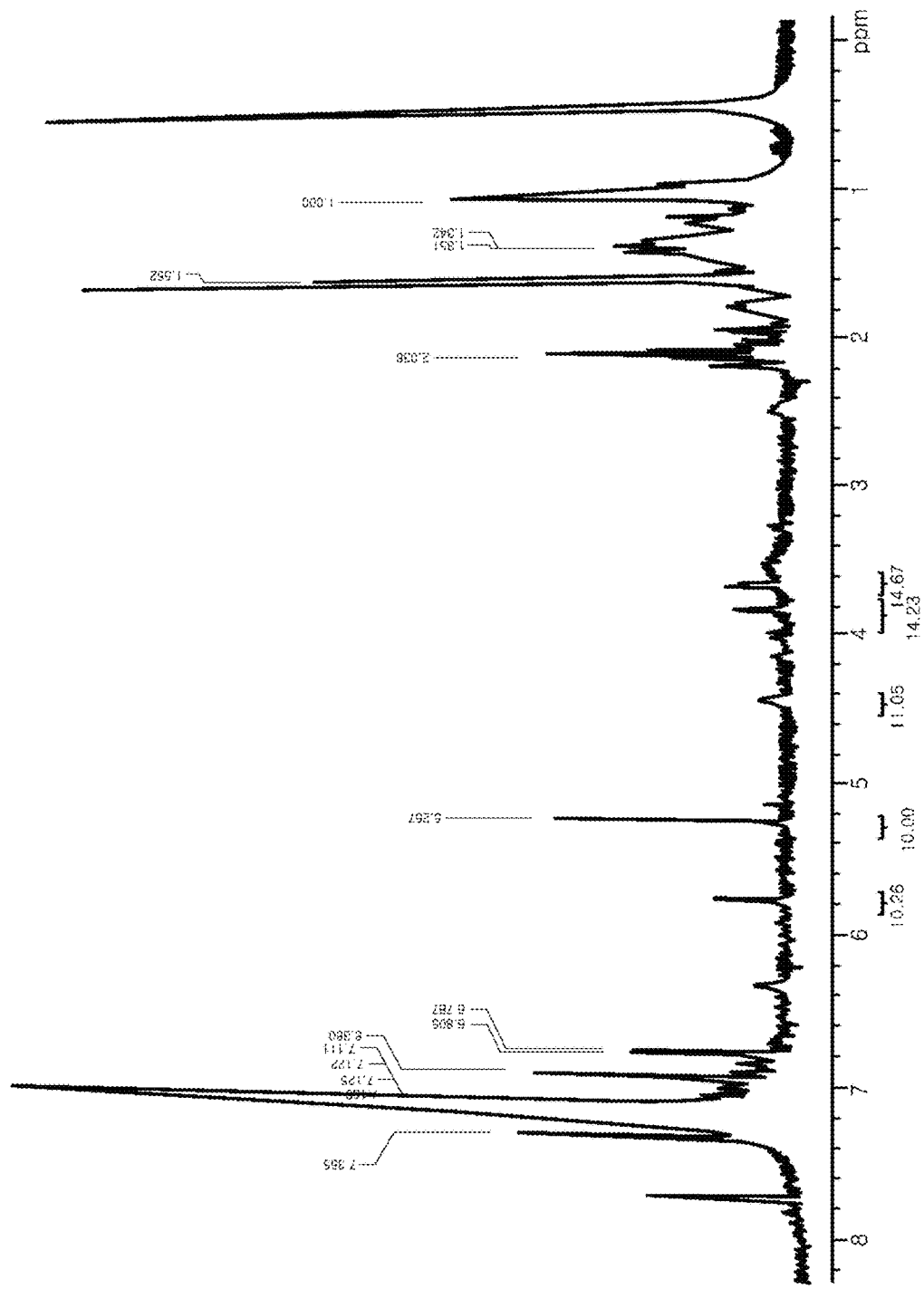
FIG. 4 is an NMR spectrum of the natural rubber obtained from the recombinant microorganism of the present invention.

NMR spectra of the dried powder extracted from the *E. coli* were recorded on Varian Mercury Plus 400 (FIG. 4). In brief, 1 ml of a specimen in benzene was loaded to a glass tube and measured for NMR at 400 MHz using an NMR spectrometer (Varian, USA). Through the measurement, H elements were analyzed to read the presence of double bonds and alkanes. The dried powder extracted from the *E. coli* was analyzed for the presence of natural rubber through peaks at retention times on NMR data. Double bond and alkane peaks identified the synthesis of natural rubber in the *E. coli*.

<Example 1-4> GPC Analysis

Figure 5:
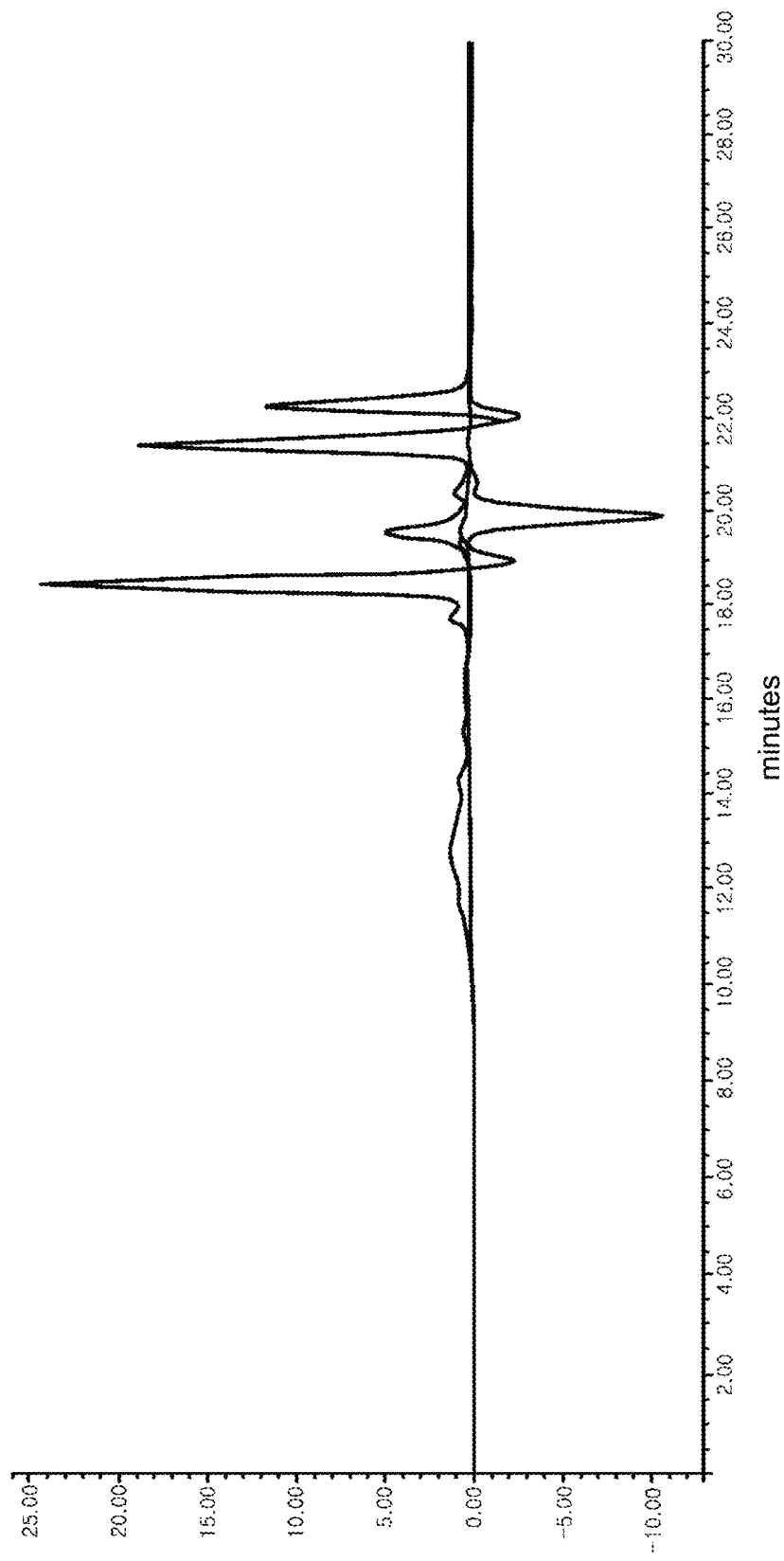
FIG. 5 is a GPC chromatogram of the natural rubber obtained from the recombinant microorganism of the present invention.

The dried powder extracted from the *E. coli* was analyzed by gel permeation chromatography (Waters HPLC isocratic 1515, detector Refractive Index 2414 USA). The dried powder extracted from the *E. coli* was dissolved in THF before analysis (FIG. 5). Analysis was performed at a flow rate of 1 ml/min, with THF serving as a mobile phase. Refractive indices thus obtained indicated the presence of a wide spectrum of polymers with an average molecular weight of 500,000. Molecular weights were determined on the basis of results identified through analysis of polymers which had a molecular weight of 10,000, 50,000, 100,000, 500,000, and 1,000,000 as reference values. For polymer analysis through GPC, a wide range of retention time was detected. The GPC analysis resulted in identifying the synthesis of a polymer having an average molecular weight of 500,000.

<Example 1-5> SEM Analysis of Natural Rubber-Producing *E. coli*

Figure 6:
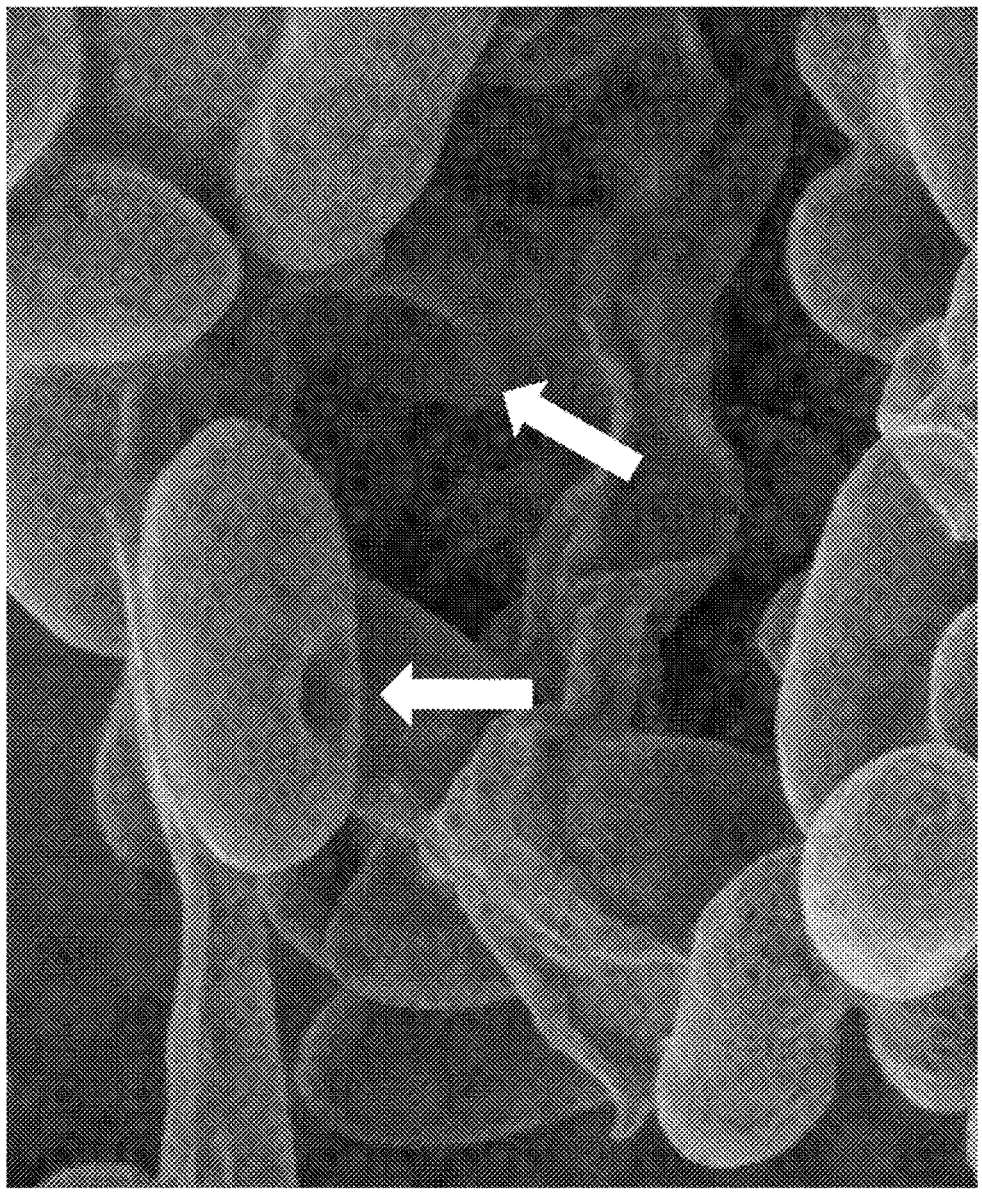
FIG. 6 is an SEM image of the recombinant microorganism *E. coli* of the present invention.
Figure 7:
FIG. 7 shows SEM images of the natural rubber obtained from the recombinant microorganism of the present invention.
Figure 7:

After being cultured for 48 hrs in 4 ml of a TB medium, the natural rubber-producing *E. coli* was morphologically analyzed under a scanning electron microscope (SEM: Model JSM 5410LV, JEOL) with magnifications for 200 nm, 1 µm, and 10 µm levels. As a result, the *E. coli* was observed to have a carved scar (indicated by an arrow in FIG. 6), which is morphologically different from typical *E. coli*. Generally, *E. coli* is rod-shaped, without indentations carved thereon. Thus, the natural rubber-producing *E. coli* developed in the present invention was understood to discharge natural rubber extracellularly. A plausible evidence of the extracellular discharge of natural rubber in the natural rubber-producing *E. coli* was a morphologically peculiar structure observed in the natural rubber-producing *E. coli* (FIG. 7). Magnification of the structure showed both two superficial types: one having streaks resulting from dryness; and the other in the form of honey before dryness.

<Example 1-6> TEM Analysis of Natural Rubber-Producing *E. coli*

Figure 8:
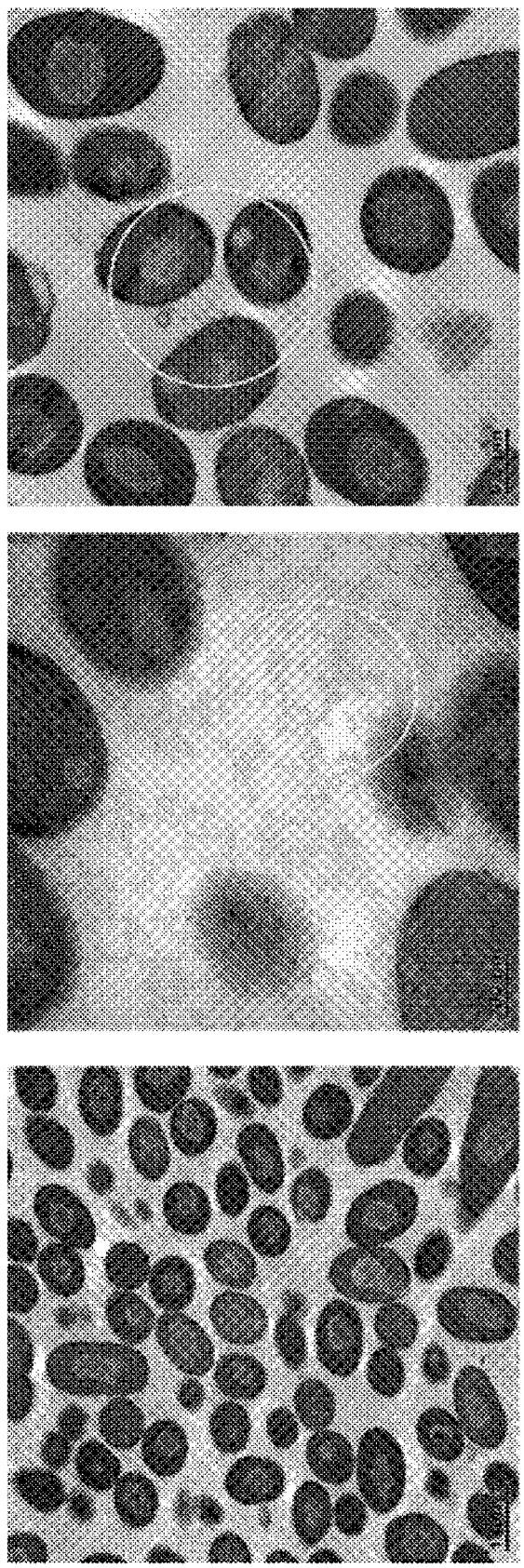
FIGS. 8 and 9 are TEM images of the recombinant microorganism *E. coli* of the present invention which is being cultured.
Figure 9:
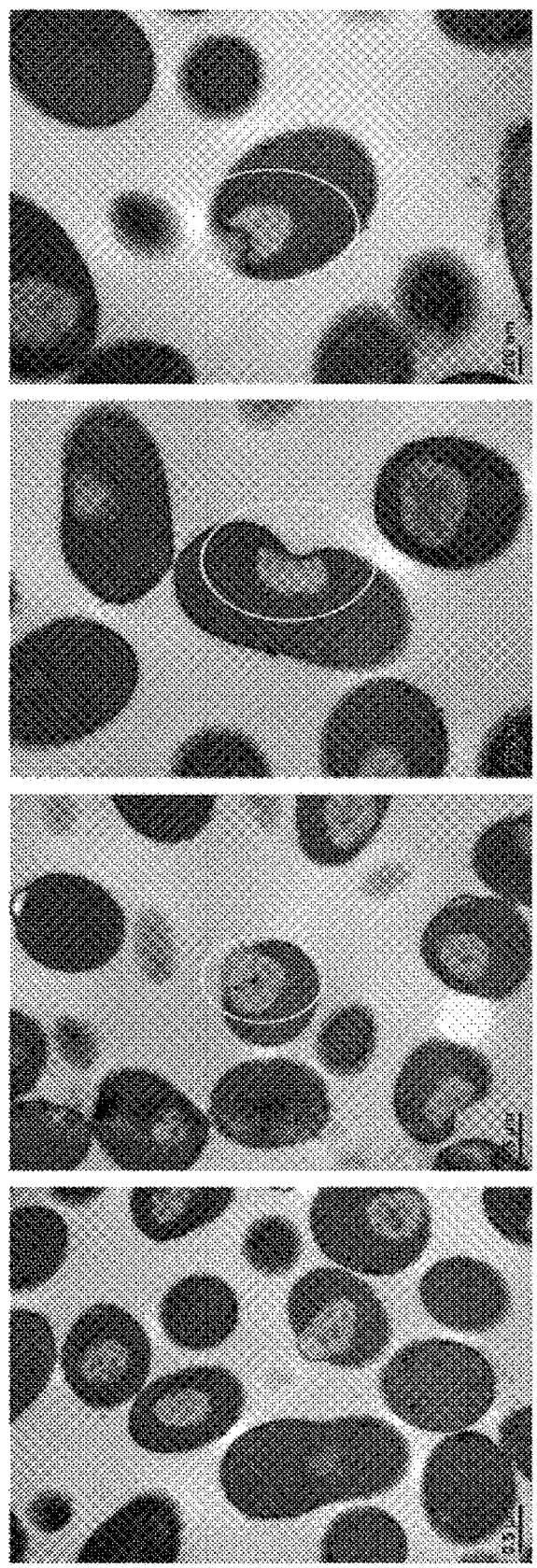

After being cultured for 48 hrs in 4 ml of a TB medium, the natural rubber-producing *E. coli* strain was observed under a transmission electron microscope (TEM: Model JEM 1010, JEOL) to analyze the intracellular structure thereof. As a result, solid structures were detected inside and outside the natural rubber-producing *E. coli* (indicated by circles in FIG. 8), but not in typical *E. coli*. In addition, the natural rubber-producing *E. coli* was observed to be extracellularly discharging natural rubber (indicated by circles in FIG. 9). Thus, the natural rubber-producing *E. coli* developed in the present invention was identified to extracellularly discharge natural rubber as well as containing natural rubber therein.

<Example 2> Production of Natural Rubber Using Recombinant Strain Having Rubber Tree-Derived Natural Rubber Synthase Gene and *E. coli*-Derived Natural Rubber Precursor Synthase Gene Introduced Thereinto The chemical synthesis of a rubber tree (*Hevea brasiliensis*)-derived gene (Genbank accession no. AY124466, SEQ ID NO: 5) encoding cis-prenyltransferase (Genbank accession no. AAM92882, SEQ ID NO: 6)), which is a natural rubber synthase of *Hevea brasiliensis*, was entrusted to COSMO Genetech (Seoul, Korea). Then, the synthesized gene was cloned into a pUCM expression vector to construct pUCM-hevea, which was under the control of the constitutive lac promoter (FIG. 1). From pUCM-hevea, the gene was amplified, together with the constitutive lac promoter and a terminator, and cloned into a pSTVM vector to construct pSTVM-hevea (FIG. 1). pSTVM-hevea was introduced, together with the pUCM-UPS carrying an *E. coli*-derived gene coding for UDP pyrophosphate synthase, constructed in Example 1-1, into *E. coli* which was then allowed to produce natural rubber.

Figure 2:
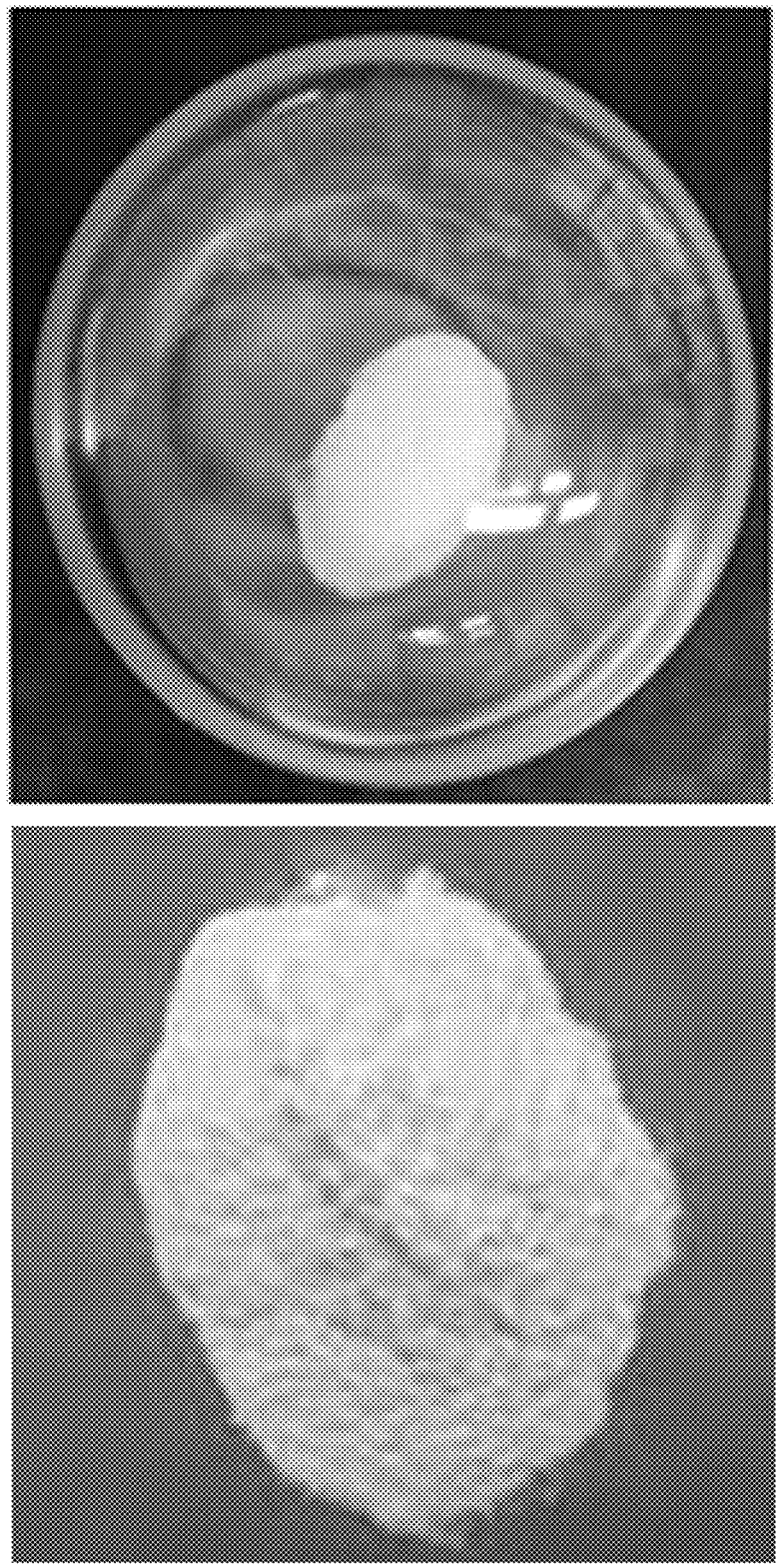
FIG. 2 shows photographic images of the natural rubber obtained from the recombinant microorganism of the present invention and the control natural rubber (polyisoprene).
Figure 10:
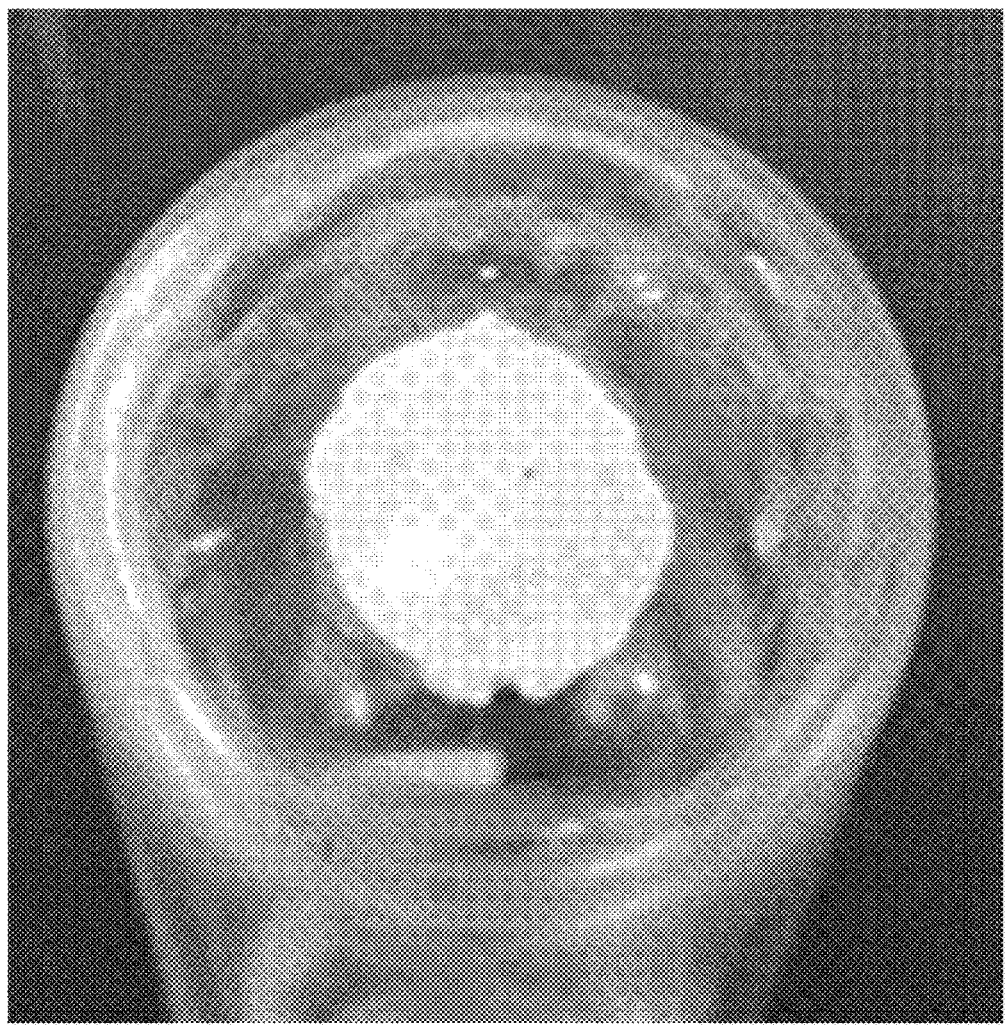
FIG. 10 is a photographic image of the natural rubber obtained according to another embodiment of the present invention.

In brief, a forward primer TCTAGAAGGAGGATTACAAAATGGAAATATATA CGGG (SEQ ID NO: 15) and a reverse primer GAATTCTTATTTTAAATATTCCTTA (SEQ ID NO: 16) which have an XbaI and an EcoRI restriction enzyme site, respectively (underlined in the sequences), were synthesized for use in cloning a *Hevea brasiliensis*-derived gene coding for the natural rubber synthase UDP pyrophosphate synthase. PCR was performed with the primers, and the PCR product was cloned into a pUCM vector using the restriction enzymes to construct pUCM-hevea. Subsequently, the forward and the reverse primer, constructed in Example 1-1 to respectively contain a HindIII and a BamHI restriction site, were used in PCR for amplifying the gene as well as the constitutive lac gene and a terminator. The PCR product thus obtained was cloned into a PSTVM vector using the restriction enzymes to construct pSTVM-hevea. Together with pUCM-UPS constructed in Example 1-1, pSTVM-hevea was introduced into *Escherichia coli* XL1-blue strain by electroporation. The transformed *E. coli* was spread on an LB agar plate containing antibiotics ampicillin (100 µg/L) and chloramphenicol (100 µg/L) and selection was made only of growing strains resistant to the antibiotics. The selected *E. coli* was inoculated into a TB medium containing tryptone 12 g/L, yeast extract 24 g/L, and glycerol 1 g/L and cultured at 30° C. and 250 rpm, as in Example 1, for 24 hrs and 48 hrs. Natural rubber was extracted using a PHB extraction method, and an image taken of the dried powder by removal of the extraction solvent is given in FIG. 10. As in FIG. 2, white powder was obtained.

<Example 3> Production of Natural Rubber According to Additional Introduction of *E. coli*-Derived Isopentenyl Isomerase <Example 3-1> Use of Guayule-Derived Natural Rubber Synthase An *E. coli*-derived gene (GenBank accession no. NC_000913.3 (REGION: 3033065 . . . 3033613), SEQ ID NO: 7) coding for *E. coli* isopentenyl diphosphate isomerase (GenBank accession no. NP_417365.1, SEQ ID NO: 8) was isolated from *E. coli*. For use in cloning the gene, a forward primer GCTCTAGAAGGAGGATTACAAAATGCAAACGGAACACGT (SEQ ID NO: 17) and a reverse primer GGAATTCTTATTTAAGCTGGGTAAATGCA (SEQ ID NO: 18) which have an XbaI and an EcoRI restriction enzyme site, respectively (underlined in the sequences), were synthesized, and the gene was amplified by PCR using the primers. The PCR product was cloned into a pBBR expression vector to construct pBBR-idi (FIG. 1).

Together with pSTVM-guauly and pUCM-UPS, both constructed in Example 1-1, pBBR-idi was introduced into *Escherichia coli* XL1-blue strain by electroporation, followed by selecting the transformed *E. coli* on an LB agar plate containing antibiotics ampicillin (100 µg/L) and chloramphenicol (100 µg/L). In this regard, the transformants were spread on LB agar plates and selection was made of growing strains. The selected *E. coli* was inoculated into a TB medium and cultured before extraction of natural rubber by a PHB extraction method. Images of the extracted natural rubber were taken and are given in FIG. 11. The extracted natural rubber was subjected to GPC analysis in the same manner as in Example 1-4, and the results are depicted in FIG. 12.

Figure 11:
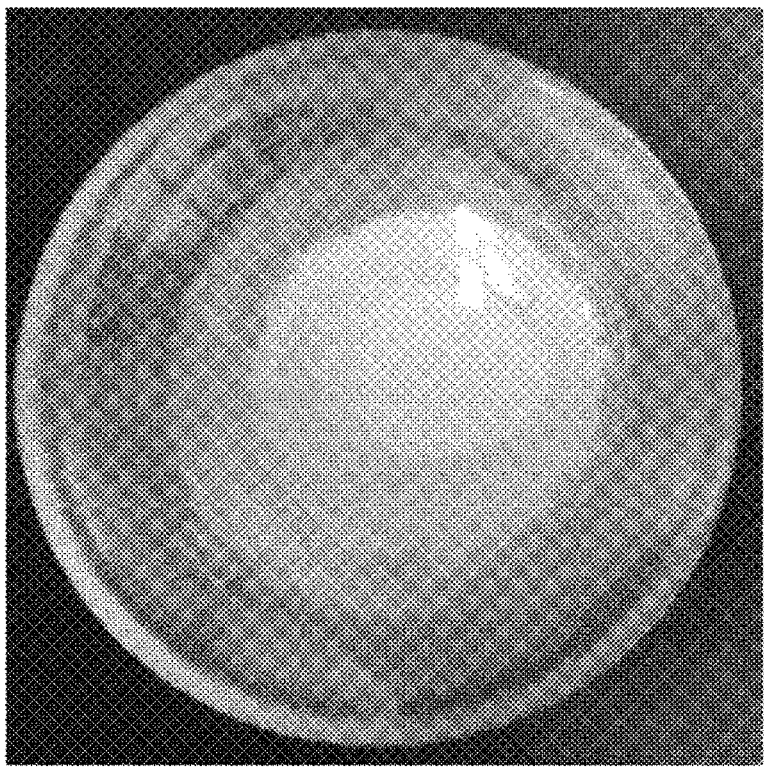
FIGS. 11 and 12 show photographic images of the natural rubber obtained according to another embodiment of the present invention, and a GPC chromatogram of the natural rubber, respectively.
Figure 11:
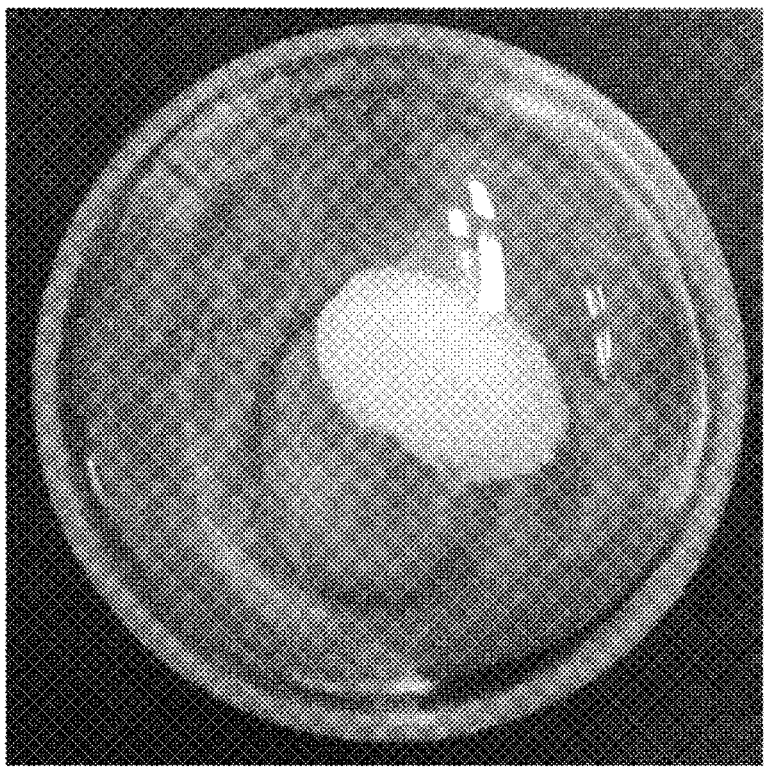
Figure 12:
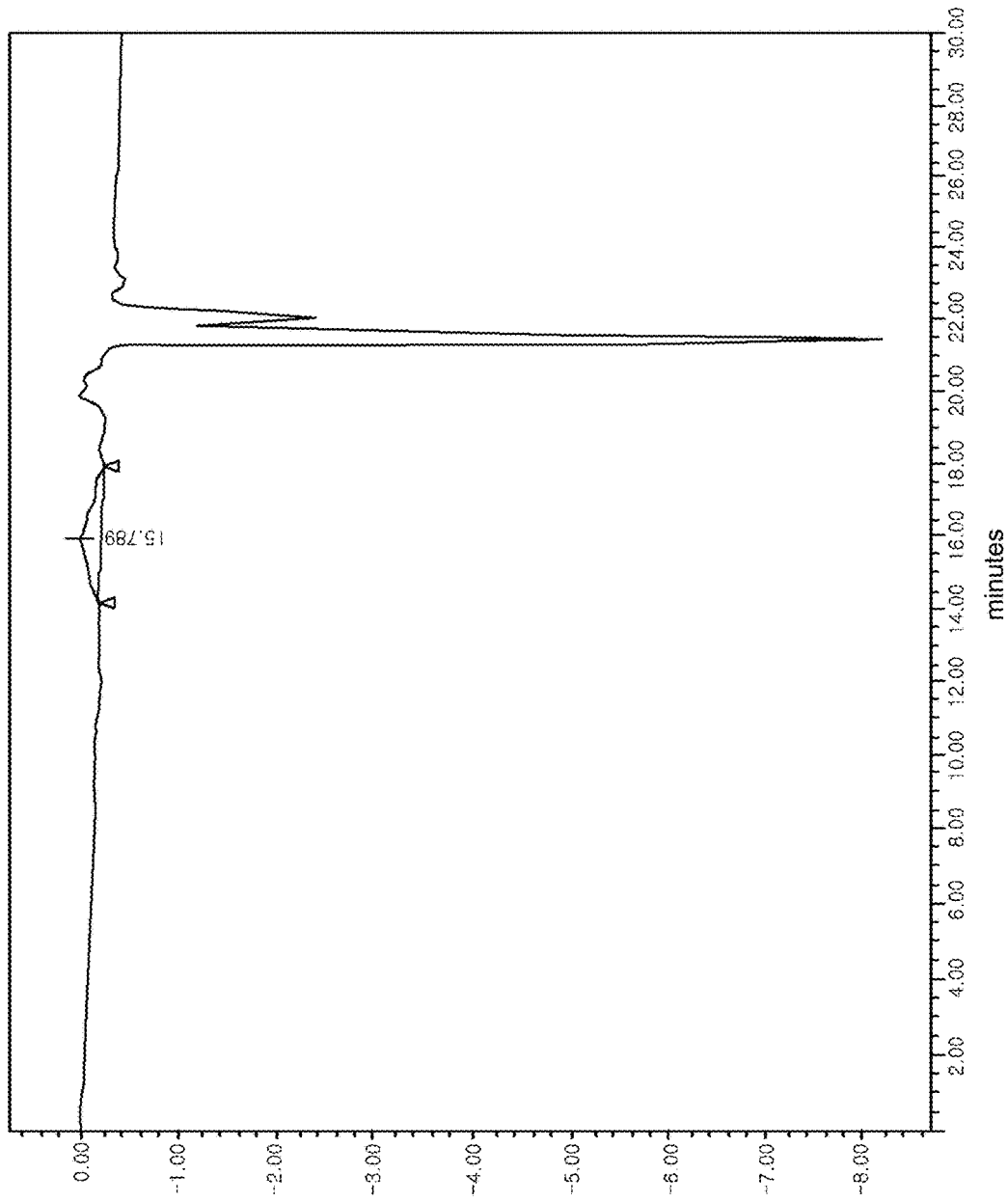

With reference to FIG. 11, white powder (left panel in FIG. 11) was identified, and observed to be significantly greater in quantity than that obtained from *E. coli* into which only pSTVM-guauly and pUCM-UPS were introduced (right panel in FIG. 11, obtained in Example 1-1). The white powder was found to have a molecular weight of 60,000 Da, as measured by GPC analysis.

<Example 3-2> Use of *Hevea brasiliensis*-Derived Natural Rubber Synthase Gene

An *E. coli* natural rubber precursor synthase gene (GenBank accession no. NC_000913 (REGION: 194906 . . . 195664), SEQ ID NO: 2), a *Hevea brasiliensis* natural rubber precursor synthase gene (Genbank accession no. AY124466, SEQ ID NO: 5), and an *E. coli* isopentenyl isomerase gene (GenBank accession no. NC_000913.3 (REGION: 3033065 . . . 3033613), SEQ ID NO: 7) were introduced into *E. coli* to produce natural rubber.

In brief, pUCM-UPS, pSTVM-hevea, and pBBR-idi, which were constructed in Examples 1-1, 2, and 3-1, respectively, were introduced together into *Escherichia coli* XL1-blue strain by electroporation, followed by selection on an LB agar plate containing antibiotics ampicillin (100 µg/L), chloramphenicol (100 µg/L) and kanamycin (100 µg/L). In the same manner as in Example 1-1, the selected *E. coli* was inoculated into a TB medium, cultured, and used to extract natural rubber by use of PHB extraction.

Figure 13:
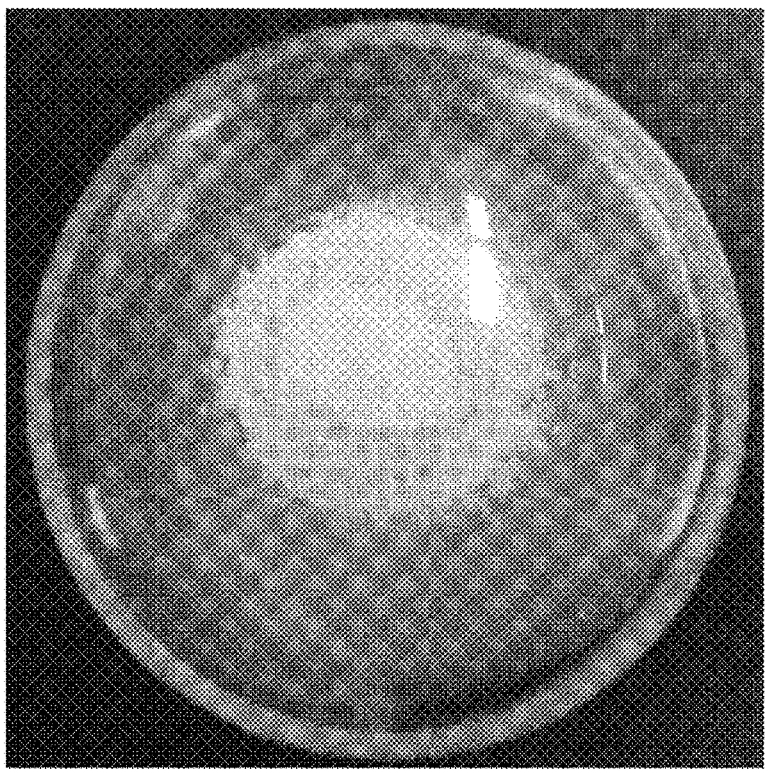
FIGS. 13 and 14 show photographic images of the natural rubber obtained according to another embodiment of the present invention, and a GPC chromatogram of the natural rubber, respectively.
Figure 13:
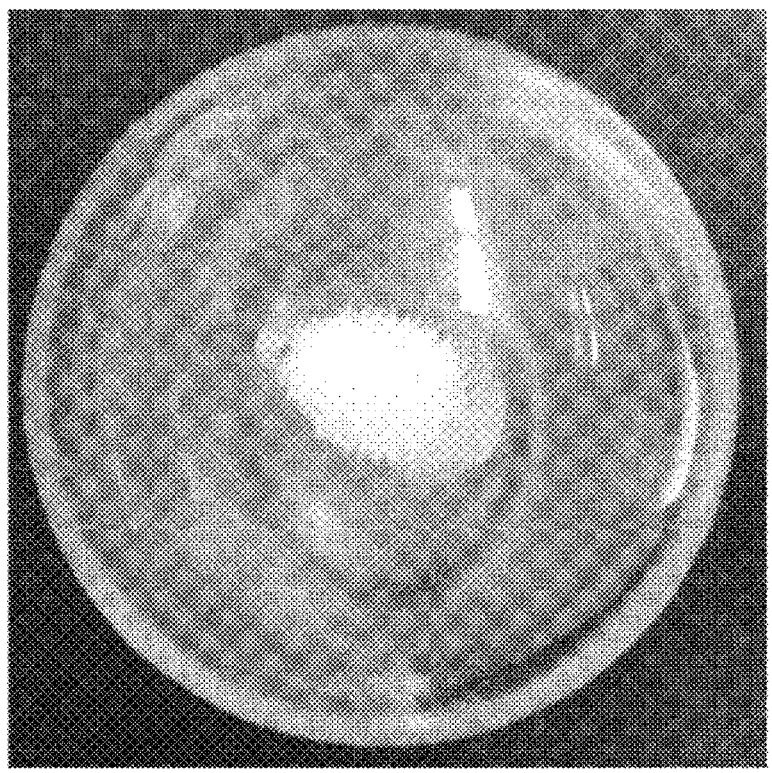
Figure 14:
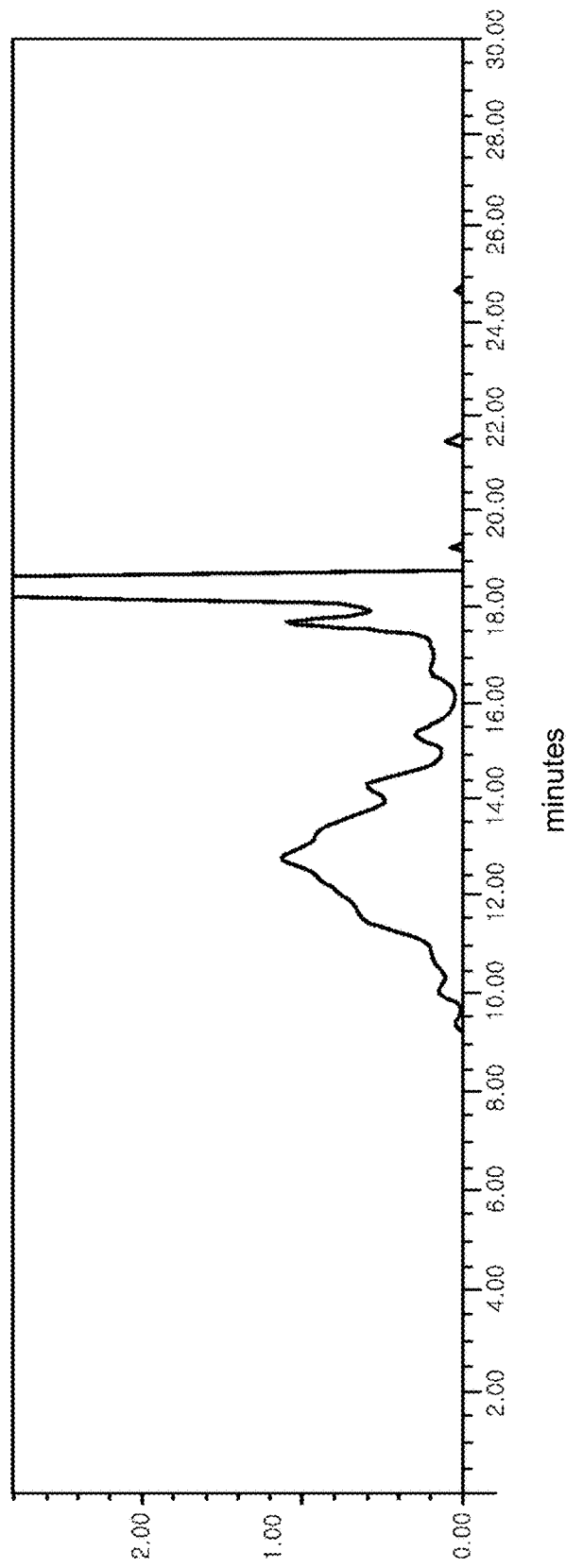

An image was taken of the extracted natural rubber and is depicted in FIG. 13. The extracted natural rubber was subjected to GPC analysis in the same manner as in Example 1-4, and the result is shown in FIG. 14. With reference to FIG. 13, white powder (left panel in FIG. 13) was identified, and observed to be significantly greater in quantity than that obtained from *E. coli* into which only pSTVM-guauly and pUCM-UPS were introduced (right panel in FIG. 13, obtained in Example 2). The white powder was found to have a molecular weight of 55,300 Da, as measured by GPC analysis.

<COMPARATIVE EXAMPLES> PRODUCTION OF NATURAL RUBBER USING RECOMBINANT STRAIN HAVING ONLY GUAYULE-DERIVED NATURAL RUBBER SYNTHASE GENE AND RUBBER TREE-DERIVED NATURAL RUBBER SYNTHASE GENE INTRODUCED THEREINTO

<Comparative Example 1> Use of Guayule-Derived Natural Rubber Synthase Gene pSTVM-guauly or pUCM-guauly into which a guayule-derived natural rubber synthase gene was cloned in Example 1-1 was introduced into *Escherichia coli* XL1-blue strain by electroporation, followed by selection on an LB agar plate containing the antibiotic chloramphenicol (100 μg/L) or ampicillin (100 μg/L). In the same manner as in Example 1-1, the selected *E. coli* was inoculated into a TB medium, cultured, and used to extract natural rubber by use of a PHB extraction method. In this case, no white powder was identified, and GPC analysis indicated the absence of a polymer compound.

<Comparative Example 2> Use of Rubber Tree-Derived Natural Rubber Synthase Gene pSTVM-hevea or pUCM-hevea into which a rubber tree-derived natural rubber synthase gene was cloned in Example 2 was introduced into *Escherichia coli* XL1-blue stain by electroporation, followed by selection on an LB agar plate containing the antibiotic chloramphenicol (100 μg/L) or ampicillin (100 μg/L). In the same manner as in Example 1-1, the selected *E. coli* was inoculated into a TB medium, cultured, and used to extract natural rubber by use of a PHB extraction method. In this case, no white powder was identified, and GPC analysis indicated the absence of a polymer compound.

Sequence List Electronic File Attachment
(A:\KIPONET\KEditor\Data\서열목록\아주대 이병진.app)

The invention claimed is:

1. A method for producing natural rubber by using a recombinant microorganism, comprising the steps of:
 (a) constructing an expression vector capable of expressing a gene encoding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, and an expression vector capable of expressing a gene encoding for an *E. coli*-derived UDP pyrophosphate synthase having the amino acid sequence of SEQ ID NO: 4;
 (b) transforming the expression vectors into a host microorganism;
 (c) culturing the transformed host microorganism; and
 (d) isolating natural rubber from a culture of the transformed host microorganism.

2. The method of claim 1, wherein the step (a) further comprises constructing an expression vector capable of expressing a gene encoding for an *E. coli*-derived isopentenyl diphosphate isomerase having the amino acid sequence of SEQ ID NO: 8, and the step (b) further comprises co-transforming the expression vector capable of expressing isopentenyl diphosphate isomerase into the host microorganism.

3. The method of claim 1, wherein the expression vector is one of a plasmid, a cosmid, a phagemid, a phage, and a virus.

4. The method of claim 1, wherein the expression vector is a plasmid.

5. The method of claim 1, wherein the expression vector includes regulatory sequences operatively linked to the genes.

6. The method of claim 1, wherein the genes are under control of a promoter selected from the group consisting of T7A1, T7A2, T7A3, λpL, λpR, lac, lacUV5, trp, tac, trc, phoA, rrnB, and 1PL.

7. The method of claim 1, wherein the expression vector further includes a selection marker gene.

8. The method of claim 1, wherein the host microorganism is a prokaryote selected from the group consisting of *Escherichia* spp., *Salmonella* spp., *Shigella* spp., *Enterobacter* spp., *Serratia* spp., *Erwinia* spp., *Serratia* spp., *Pseudomonas* spp., *Caulobacter* spp., *Synechocystis* spp., *Synechococcus* spp., *Bacillus* spp., *Lactococcus* spp., *Streptomyces* spp., *Rhodococcus* spp., *Corynebacterium* spp., and *Mycobacterium* spp.

9. The method of claim 8, wherein the *Synechocystis* spp. is *Synechocystis* species PCC 6803 or *Synechocystis* species PCC 6301, the *Bacillus* spp. is *Bacillus brevis*, *Bacillus subtilis*, or *Bacillus thuringienesis*, the *Lactococcus* spp. is *Lactococcus lactis*, the *Streptomyces* spp. is *Streptomyces lividans*, *Streptomyces ambofaciens*, *Streptomyces fradiae*, or *Streptomyces griseofuscus*, the *Rhodococcus* spp. is *Rhodococcus erythropolis*, the *Corynebacterium* spp. is *Corynebacterium gluamicum*, and the *Mycobacterium* spp. is *Mycobacterium smegmatis*.

10. The method of claim 1, wherein the microorganism is *E. coli*.

11. A method for producing natural rubber by using a recombinant microorganism, comprising the steps of:
 (a) constructing an expression vector capable of expressing a gene encoding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, and a gene encoding for an *E. coli*-derived UDP pyrophosphate synthase having the amino acid sequence of SEQ ID NO: 4;
 (b) transforming the expression vector into a host microorganism;
 (c) culturing the transformed host microorganism; and
 (d) isolating natural rubber from a culture of the transformed host microorganism.

12. The method of claim 11, wherein the expression vector is capable of further expressing a gene encoding for *E. coli*-derived isopentenyl diphosphate isomerase having the amino acid sequence of SEQ ID NO: 8.

13. The method of claim 11, wherein the host microorganism is *E. coli*.

14. A recombinant microorganism, transformed with (i) a gene encoding for cis-prenyltransferase, which is a guayule-derived natural rubber synthase having the amino acid sequence of SEQ ID NO: 2 or a *Hevea brasiliensis*-derived natural rubber synthase having the amino acid sequence of SEQ ID NO: 6, and a gene encoding for UDP pyrophosphate synthase, which is an *E. coli*-derived natural rubber precursor synthase having the amino acid sequence of SEQ ID NO: 4 and capable of expressing the cis-prenyltransferase gene and the UDP pyrophosphate synthase gene.

15. The recombinant microorganism of claim 14, wherein the recombinant microorganism is further transformed with a gene encoding for *E. coli*-derived isopentenyl diphosphate isomerase having the amino acid sequence of SEQ ID NO: 8 so as to express the gene.

16. The recombinant microorganism of claim 14, wherein the microorganism is *E. coli*.

* * * * *

SEQUENCE LISTING

```
<160> NUMBER OF SEQ ID NOS: 18

<210> SEQ ID NO 1
<211> LENGTH: 726
<212> TYPE: DNA
<213> ORGANISM: Parthenium argentatum

<400> SEQUENCE: 1
atggccgaac ctgaatccaa tcagtccgcc cagcccgtgg cagagaggga tgggggagag      60
gagcaactgc atctgaaata tcttgatttt gtgcaaaacg ctgtgatcta ttttgttgtt     120
tgtttctcta ctgtttacgg ttacgcaaag gagaacgccg gttcgtggaa gcctggtgtt     180
caaaccgttg agaacaccgt tctaaacgtc gttggaccgg tttacgaaaa gtattatgac     240
tatcctatag aggccctcaa gttccttgat gtaaaggtgg gcgacttggt gaccgagctg     300
aaacggcacg tgccatcact aatgaaacag gcttcaagcc aagccaaata cacggctcag     360
aaccttccag aagtggctaa agccttggca acagaggcat tcaaaactgc tacaaatgtg     420
gccaacacat tgtacgtaaa atgcgagcca acagctaaac agctatacat gaactacgag     480
ccggtagctg agaaatacac ggtgtcgaca tggcggtcat tgaacaaact cccctttgttt    540 cctcaggtag ctcagattgc ggttcctact ggtgcttatg tgcttgagaa gtataacgac     600
cccgttagct acactgcgga caaaggttat gctgtggctc agtatttacc gttggttccg     660
attgataaaa ttgctaaggt gtttaaaaag ggtgagagcg ggtcaacggt tggtcaaagt     720
ggttag                                                               726

<210> SEQ ID NO 2
<211> LENGTH: 241
<212> TYPE: PRT
<213> ORGANISM: Parthenium argentatum

<400> SEQUENCE: 2

Met Ala Glu Pro Glu Ser Asn Gln Ser Ala Gln Pro Val Ala Glu Arg
  1               5                  10                  15

Asp Gly Gly Glu Glu Gln Leu His Leu Lys Tyr Leu Asp Phe Val Gln
             20                  25                  30

Asn Ala Val Ile Tyr Phe Val Val Cys Phe Ser Thr Val Tyr Gly Tyr
         35                  40                  45
```

| | | | | | | | | | | | |
|---|---|---|---|---|---|---|---|---|---|---|---|
| Ala | Lys | Glu | Asn | Ala | Gly | Ser | Trp | Lys | Pro | Gly | Val | Gln | Thr | Val | Glu |
| | 50 | | | | 55 | | | | 60 | | |

Ala Lys Glu Asn Ala Gly Ser Trp Lys Pro Gly Val Gln Thr Val Glu
            50                  55                  60

Asn Thr Val Leu Asn Val Val Gly Pro Val Tyr Glu Lys Tyr Tyr Asp
 65                  70                  75                  80

Tyr Pro Ile Glu Ala Leu Lys Phe Leu Asp Val Lys Val Gly Asp Leu
                 85                  90                  95

Val Thr Glu Leu Lys Arg His Val Pro Ser Leu Met Lys Gln Ala Ser
                100                 105                 110

Ser Gln Ala Lys Tyr Thr Ala Gln Asn Leu Pro Glu Val Ala Lys Ala
                115                 120                 125

Leu Ala Thr Glu Ala Phe Lys Thr Ala Thr Asn Val Ala Asn Thr Leu
        130                 135                 140

Tyr Val Lys Cys Glu Pro Thr Ala Lys Gln Leu Tyr Met Asn Tyr Glu
145                 150                 155                 160

Pro Val Ala Glu Lys Tyr Thr Val Ser Thr Trp Arg Ser Leu Asn Lys
                165                 170                 175

Leu Pro Leu Phe Pro Gln Val Ala Gln Ile Ala Val Pro Thr Gly Ala
                180                 185                 190

Tyr Val Leu Glu Lys Tyr Asn Asp Pro Val Ser Tyr Thr Ala Asp Lys
                195                 200                 205

Gly Tyr Ala Val Ala Gln Tyr Leu Pro Leu Val Pro Ile Asp Lys Ile
        210                 215                 220

Ala Lys Val Phe Lys Lys Gly Glu Ser Gly Ser Thr Val Gly Gln Ser
225                 230                 235                 240

Gly

<210> SEQ ID NO 3
<211> LENGTH: 759
<212> TYPE: DNA
<213> ORGANISM: Escherichia coli

<400> SEQUENCE: 3

```
atgttgtctg ctactcaacc acttagcgaa aaattgccag cgcatggctg ccgtcatgtt      60
gcgatcatta tggacggcaa tggccgctgg gcaaaaaagc aagggaagat tcgtgccttt     120
gggcataaag ccggggcaaa atccgtccgc cgggctgtct cttttgcggc caacaacggt     180
attgaggcgt taacgctgta tgcctttagt agtgaaaact ggaaccgacc agcgcaggaa     240
gtcagtgcgt taatggaact gttttgtgtgg cgctcgata gcgaagtaaa aagtctgcac     300
cgacataacg tgcgtctgcg tattattggc gataccagtc gctttaactc gcgtttgcaa     360
gaacgtattc gtaaatctga agcgctaaca gccgggaata ccggtctgac gctgaatatt     420
gcggcgaact acggtggacg ttgggatata gtccagggag tcaggcaact ggctgaaaag     480
gtgcagcaag gaaacctgca accagatcag atagatgaag agatgctaaa ccagcatgtc     540
tgtatgcatg aactggcccc tgtagattta gtaattagga ctgggggggga gcatcgcatt     600
agtaacttt tgctttggca aattgcctat gccgaacttt actttacaga tgttctctgg     660
cccgatttcg atgaacaaga ctttgaaggg gcgttaaatg cctttgctaa tcgagagcgt     720
cgtttcggcg gcaccgagcc cggtgatgaa acagcctga                           759
```

<210> SEQ ID NO 4
<211> LENGTH: 252
<212> TYPE: PRT
<213> ORGANISM: Escherichia coli

<400> SEQUENCE: 4

```
Met Leu Ser Ala Thr Gln Pro Leu Ser Glu Lys Leu Pro Ala His Gly
1               5                   10                  15

Cys Arg His Val Ala Ile Ile Met Asp Gly Asn Gly Arg Trp Ala Lys
                20                  25                  30

Lys Gln Gly Lys Ile Arg Ala Phe Gly His Lys Ala Gly Ala Lys Ser
            35                  40                  45

Val Arg Arg Ala Val Ser Phe Ala Ala Asn Asn Gly Ile Glu Ala Leu
        50                  55                  60

Thr Leu Tyr Ala Phe Ser Ser Glu Asn Trp Asn Arg Pro Ala Gln Glu
65                  70                  75                  80

Val Ser Ala Leu Met Glu Leu Phe Val Trp Ala Leu Asp Ser Glu Val
                85                  90                  95

Lys Ser Leu His Arg His Asn Val Arg Leu Arg Ile Ile Gly Asp Thr
            100                 105                 110

Ser Arg Phe Asn Ser Arg Leu Gln Glu Arg Ile Arg Lys Ser Glu Ala
        115                 120                 125

Leu Thr Ala Gly Asn Thr Gly Leu Thr Leu Asn Ile Ala Ala Asn Tyr
130                 135                 140

Gly Gly Arg Trp Asp Ile Ile Gln Gly Val Arg Gln Leu Ala Glu Lys
145                 150                 155                 160

Val Gln Gln Gly Asn Leu Gln Pro Asp Gln Ile Asp Glu Glu Met Leu
                165                 170                 175

Asn Gln His Val Cys Met His Glu Leu Ala Pro Val Asp Leu Val Ile
            180                 185                 190

Arg Thr Gly Gly Glu His Arg Ile Ser Asn Phe Leu Leu Trp Gln Ile
        195                 200                 205

Ala Tyr Ala Glu Leu Tyr Phe Thr Asp Val Leu Trp Pro Asp Phe Asp
210                 215                 220

Glu Gln Asp Phe Glu Gly Ala Leu Asn Ala Phe Ala Asn Arg Glu Arg
225                 230                 235                 240

Arg Phe Gly Gly Thr Glu Pro Gly Asp Glu Thr Ala
                245                 250
```

<210> SEQ ID NO 5
<211> LENGTH: 891
<212> TYPE: DNA
<213> ORGANISM: Hevea brasiliensis

<400> SEQUENCE: 5

```
atggaaatat atacgggtca gaggccaagt gtgtttagaa ttttttgggaa atacatgaga    60
aaagggttat atagcatcct aacccaaggt cccatcccta ctcatcttgc cttcataatg   120
gatggaaacc ggaggtttgc taagaagcat aaaatgaaag aagcagaagg ttataaggca   180
ggatatttag ctcttctgag aacactaact tattgctatg agttgggagt gaggtatgta   240
accatttatg cctttagcat tgataatttt cgaaggcaac ctcgtgaggt tcagtgcgta   300
atgaatctaa tgatggagaa gattgaagag attatcgtgg aagaaagtat catgaatgca   360
tatgatgttg gcgtacgtat tgtgggtaac ctgaatcttt tagatgagcc aatcaggatc   420
gcagcagaaa agattatgag ggctactgcc aataattcca ggtttgtgct tctcattgct   480
gtagcctata gttcaactga tgagatcgtg catgctgttg aagaatcctc taaagacaaa   540
ttgaactcca atgaagtttg caacaatggg attgaagctg aacaagaatt taaggaggca   600
aacggaactg gaaacagtgt gattccagtt cagaagacgg agtcatattc tggaataaat   660
```

```
cttgcagacc ttgagaaaaa cacctacgta atcctcatc ctgatgtctt gattcgaact    720
tctgggttga gccgtctaag taactaccta ctttggcaga ctagtaattg catactgtat    780
tctccttttg cactgtggcc agagattggt ctcaggcact tggtatggac agtaatgaac    840
ttccaacgtc atcattctta tttggagaag cataaggaat atttaaaata a             891
```

<210> SEQ ID NO 6
<211> LENGTH: 296
<212> TYPE: PRT
<213> ORGANISM: Hevea brasiliensis

<400> SEQUENCE: 6

```
Met Glu Ile Tyr Thr Gly Gln Arg Pro Ser Val Phe Arg Ile Phe Gly
 1               5                  10                  15
Lys Tyr Met Arg Lys Gly Leu Tyr Ser Ile Leu Thr Gln Gly Pro Ile
                20                  25                  30
Pro Thr His Leu Ala Phe Ile Met Asp Gly Asn Arg Arg Phe Ala Lys
            35                  40                  45
Lys His Lys Met Lys Glu Ala Glu Gly Tyr Lys Ala Gly Tyr Leu Ala
        50                  55                  60
Leu Leu Arg Thr Leu Thr Tyr Cys Tyr Glu Leu Gly Val Arg Tyr Val
65                  70                  75                  80
Thr Ile Tyr Ala Phe Ser Ile Asp Asn Phe Arg Arg Gln Pro Arg Glu
                85                  90                  95
Val Gln Cys Val Met Asn Leu Met Met Glu Lys Ile Glu Glu Ile Ile
            100                 105                 110
Val Glu Glu Ser Ile Met Asn Ala Tyr Asp Val Gly Val Arg Ile Val
        115                 120                 125
Gly Asn Leu Asn Leu Leu Asp Glu Pro Ile Arg Ile Ala Ala Glu Lys
    130                 135                 140
Ile Met Arg Ala Thr Ala Asn Asn Ser Arg Phe Val Leu Leu Ile Ala
145                 150                 155                 160
Val Ala Tyr Ser Ser Thr Asp Glu Ile Val His Ala Val Glu Glu Ser
                165                 170                 175
Ser Lys Asp Lys Leu Asn Ser Asn Glu Val Cys Asn Asn Gly Ile Glu
            180                 185                 190
Ala Glu Gln Glu Phe Lys Glu Ala Asn Gly Thr Gly Asn Ser Val Ile
        195                 200                 205
Pro Val Gln Lys Thr Glu Ser Tyr Ser Gly Ile Asn Leu Ala Asp Leu
    210                 215                 220
Glu Lys Asn Thr Tyr Val Asn Pro His Pro Asp Val Leu Ile Arg Thr
225                 230                 235                 240
Ser Gly Leu Ser Arg Leu Ser Asn Tyr Leu Leu Trp Gln Thr Ser Asn
                245                 250                 255
Cys Ile Leu Tyr Ser Pro Phe Ala Leu Trp Pro Glu Ile Gly Leu Arg
            260                 265                 270
His Leu Val Trp Thr Val Met Asn Phe Gln Arg His His Ser Tyr Leu
        275                 280                 285
Glu Lys His Lys Glu Tyr Leu Lys
    290                 295
```

<210> SEQ ID NO 7
<211> LENGTH: 549
<212> TYPE: DNA
<213> ORGANISM: Escherichia coli

<400> SEQUENCE: 7

```
atgcaaacgg aacacgtcat tttattgaat gcacagggag ttcccacggg tacgctggaa      60
aagtatgccg cacacacggc agacacccgc ttacatctcg cgttctccag ttggctgttt     120
aatgccaaag acaattatt agttacccgc cgcgcactga gcaaaaaagc atggcctggc     180
gtgtggacta actcggtttg tgggcaccca caactgggag aaagcaacga agacgcagtg     240
atccgccgtt gccgttatga gcttggcgtg gaaattacgc ctcctgaatc tatctatcct     300
gactttcgct accgcgccac cgatccgagt ggcattgtgg aaaatgaagt gtgtccggta     360
tttgccgcac gcaccactag tgcgttacag atcaatgatg atgaagtgat ggattatcaa     420
tggtgtgatt tagcagatgt attacacggt attgatgcca cgccgtgggc gttcagtccg     480
tggatggtga tgcaggcgac aaatcgcgaa gccagaaaac gattatctgc atttacccag     540
cttaaataa                                                              549
```

<210> SEQ ID NO 8
<211> LENGTH: 182
<212> TYPE: PRT
<213> ORGANISM: Escherichia coli

<400> SEQUENCE: 8

```
Met Gln Thr Glu His Val Ile Leu Leu Asn Ala Gln Gly Val Pro Thr
1               5                   10                  15
Gly Thr Leu Glu Lys Tyr Ala Ala His Thr Ala Asp Thr Arg Leu His
            20                  25                  30
Leu Ala Phe Ser Ser Trp Leu Phe Asn Ala Lys Gly Gln Leu Leu Val
        35                  40                  45
Thr Arg Arg Ala Leu Ser Lys Lys Ala Trp Pro Gly Val Trp Thr Asn
    50                  55                  60
Ser Val Cys Gly His Pro Gln Leu Gly Glu Ser Asn Glu Asp Ala Val
65                  70                  75                  80
Ile Arg Arg Cys Arg Tyr Glu Leu Gly Val Glu Ile Thr Pro Pro Glu
                85                  90                  95
Ser Ile Tyr Pro Asp Phe Arg Tyr Arg Ala Thr Asp Pro Ser Gly Ile
            100                 105                 110
Val Glu Asn Glu Val Cys Pro Val Phe Ala Ala Arg Thr Thr Ser Ala
        115                 120                 125
Leu Gln Ile Asn Asp Asp Glu Val Met Asp Tyr Gln Trp Cys Asp Leu
    130                 135                 140
Ala Asp Val Leu His Gly Ile Asp Ala Thr Pro Trp Ala Phe Ser Pro
145                 150                 155                 160
Trp Met Val Met Gln Ala Thr Asn Arg Glu Ala Arg Lys Arg Leu Ser
                165                 170                 175
Ala Phe Thr Gln Leu Lys
            180
```

<210> SEQ ID NO 9
<211> LENGTH: 27
<212> TYPE: DNA
<213> ORGANISM: Artificial Sequence
<220> FEATURE:
<223> OTHER INFORMATION: primer

<400> SEQUENCE: 9

```
gccgtctaga aggaggatta caaaatg                                          27
```

```
<210> SEQ ID NO 10
<211> LENGTH: 19
<212> TYPE: DNA
<213> ORGANISM: Artificial Sequence
<220> FEATURE:
<223> OTHER INFORMATION: primer

<400> SEQUENCE: 10
ggaattctca ggtgtttca                                                  19

<210> SEQ ID NO 11
<211> LENGTH: 37
<212> TYPE: DNA
<213> ORGANISM: Artificial Sequence
<220> FEATURE:
<223> OTHER INFORMATION: primer

<400> SEQUENCE: 11
tctagaagga ggattacaaa atggccgaac ctgaatc                              37

<210> SEQ ID NO 12
<211> LENGTH: 26
<212> TYPE: DNA
<213> ORGANISM: Artificial Sequence
<220> FEATURE:
<223> OTHER INFORMATION: primer

<400> SEQUENCE: 12
gaattcctaa ccactttgac caaccg                                          26

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
cccaagcttc cgactggaaa gcg                                             23

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
cgggatcccg gtgtgaaata ccg                                             23

<210> SEQ ID NO 15
<211> LENGTH: 37
<212> TYPE: DNA
<213> ORGANISM: Artificial Sequence
<220> FEATURE:
<223> OTHER INFORMATION: primer

<400> SEQUENCE: 15
tctagaagga ggattacaaa atggaaatat atacggg                              37

<210> SEQ ID NO 16
<211> LENGTH: 25
<212> TYPE: DNA
<213> ORGANISM: Artificial Sequence
<220> FEATURE:
<223> OTHER INFORMATION: primer
```

```
<400> SEQUENCE: 16
gaattcttat tttaaatatt cctta                                              25

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
gctctagaag gaggattaca aaatgcaaac ggaacacgt                                39

<210> SEQ ID NO 18
<211> LENGTH: 29
<212> TYPE: DNA
<213> ORGANISM: Artificial Sequence
<220> FEATURE:
<223> OTHER INFORMATION: primer

<400> SEQUENCE: 18
ggaattctta tttaagctgg gtaaatgca                                          29
```